(12) United States Patent
Oshima

(10) Patent No.: US 10,881,556 B2
(45) Date of Patent: Jan. 5, 2021

(54) ABSORBENT ARTICLE HAVING A CAVITY PORTION AND A PROJECTION THAT FITS IN THE CAVITY PORTION

(71) Applicant: DAIO PAPER CORPORATION, Ehime (JP)

(72) Inventor: Aya Oshima, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 472 days.

(21) Appl. No.: 15/757,759

(22) PCT Filed: Sep. 5, 2016

(86) PCT No.: PCT/JP2016/075996
§ 371 (c)(1),
(2) Date: Mar. 6, 2018

(87) PCT Pub. No.: WO2017/047429
PCT Pub. Date: Mar. 23, 2017

(65) Prior Publication Data
US 2018/0344540 A1 Dec. 6, 2018

(30) Foreign Application Priority Data

Sep. 15, 2015 (JP) .................................. 2015-181530

(51) Int. Cl.
*A61F 13/533* (2006.01)
*A61F 13/532* (2006.01)
(Continued)

(52) U.S. Cl.
CPC .......... *A61F 13/533* (2013.01); *A61F 13/532* (2013.01); *A61F 13/15804* (2013.01);
(Continued)

(58) Field of Classification Search
CPC .... A61F 13/533; A61F 13/535; A61F 13/532; A61F 13/534; A61F 2013/5355;
(Continued)

(56) References Cited

U.S. PATENT DOCUMENTS 7,504,552 B2 * 3/2009 Tamura ............... A61F 13/4704
604/380
7,547,815 B2 * 6/2009 Ohashi ............... A61F 13/4704
604/378
(Continued)

FOREIGN PATENT DOCUMENTS

EP 2656826 10/2013
JP H10-314217 12/1998
(Continued)

OTHER PUBLICATIONS

International Search Report for PCT/JP2016/075996 dated Dec. 6, 2016.

*Primary Examiner* — Michele M Kidwell
(74) *Attorney, Agent, or Firm* — IPUSA, PLLC

(57) ABSTRACT

In an absorbent article (200), a pair of slits (40) each extending in a front and rear direction with a predetermined width is formed in an absorbent body (23) at a front and rear direction region at least at a crotch portion (C2) such that to section a first portion (11) at middle, and a second portion (12) and a third portion (12) at both sides of the first portion in a width direction, respectively, projection portions (23P) projected toward both sides in the width direction at middle in the front and rear direction of the first portion (11) are included in the absorbent body, and cavity portions (23D) in which the projection portions (23P) fit outwardly in the width direction are formed at a front and rear direction position corresponding to the projection portions (23P) in the second portion (12) and the third portion (12), respectively.

2 Claims, 20 Drawing Sheets

(51) Int. Cl.
*A61F 13/15* (2006.01)
*A61F 13/53* (2006.01)
*A61F 13/531* (2006.01)

(52) U.S. Cl.
CPC ............... *A61F 2013/5312* (2013.01); *A61F 2013/530868* (2013.01)

(58) Field of Classification Search
CPC .... A61F 13/53436; A61F 2013/530868; A61F 2013/530875; A61F 2013/530883; A61F 13/49001; A61F 2013/530861; A61F 2013/4568; A61F 2013/4581; A61F 13/536; A61F 13/5323; A61F 13/5326; A61F 13/4756; A61F 13/4704
See application file for complete search history.

(56) References Cited

U.S. PATENT DOCUMENTS

| | | | | |
|---|---|---|---|---|
| 9,445,950 | B2 * | 9/2016 | Mukai | A61F 13/49001 |
| 2003/0143376 | A1 | 7/2003 | Toyoshima et al. | |
| 2006/0069371 | A1 * | 3/2006 | Ohashi | A61F 13/476 604/385.01 |
| 2006/0264859 | A1 * | 11/2006 | Tsuji | A61F 13/49012 604/385.28 |
| 2008/0140042 | A1 * | 6/2008 | Mukai | A61F 13/49001 604/385.23 |
| 2010/0063470 | A1 | 3/2010 | Suzuki et al. | |
| 2010/0069874 | A1 * | 3/2010 | Noda | A61F 13/4758 604/385.23 |
| 2019/0046367 | A1 * | 2/2019 | Oshima | A61F 13/533 |
| 2019/0060140 | A1 * | 2/2019 | Oshima | A61F 13/533 |

FOREIGN PATENT DOCUMENTS

| | | | | |
|---|---|---|---|---|
| JP | 2003-250836 | | 9/2003 | |
| JP | 2005-185616 | | 7/2005 | |
| JP | 2012-040259 | | 3/2012 | |
| JP | 2012-157380 | | 8/2012 | |
| JP | 2015-039579 | | 3/2015 | |
| WO | 2012/029848 | * | 3/2012 | ............ A61F 13/15 |

* cited by examiner

FIG.4
(a)
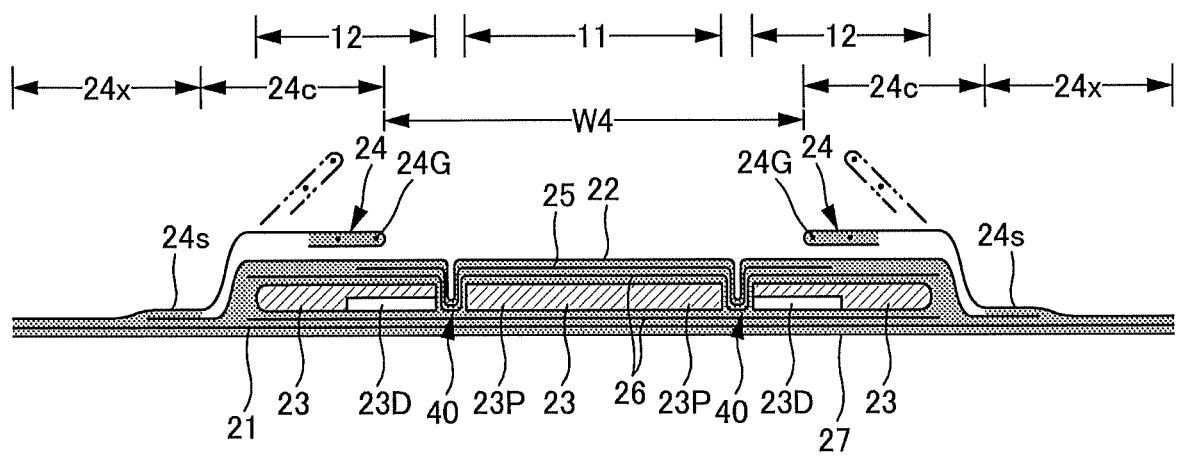
(b)
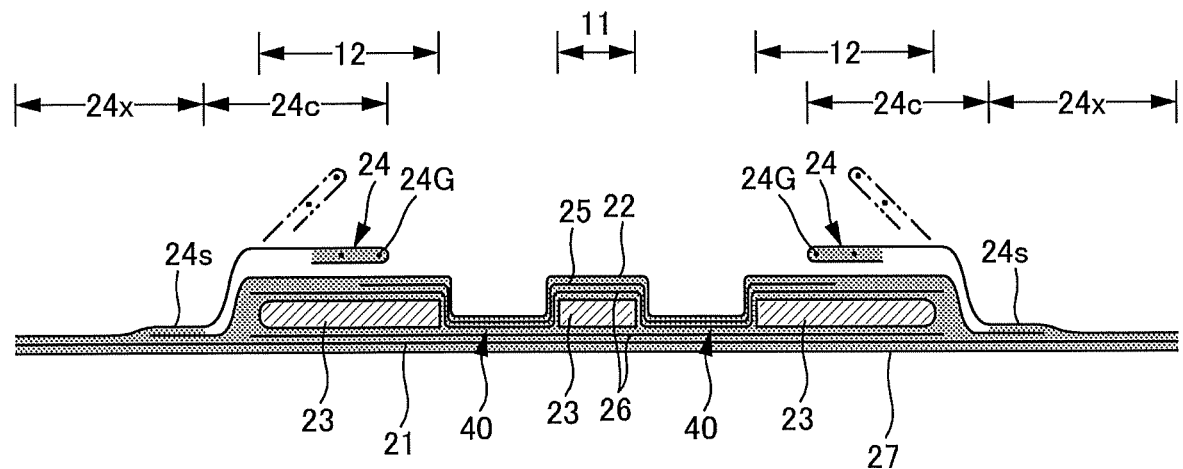

FIG.5
(a)
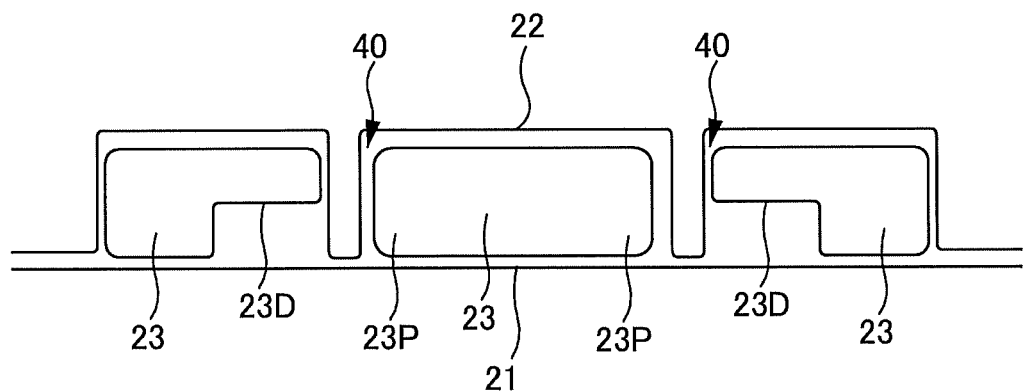
(b)
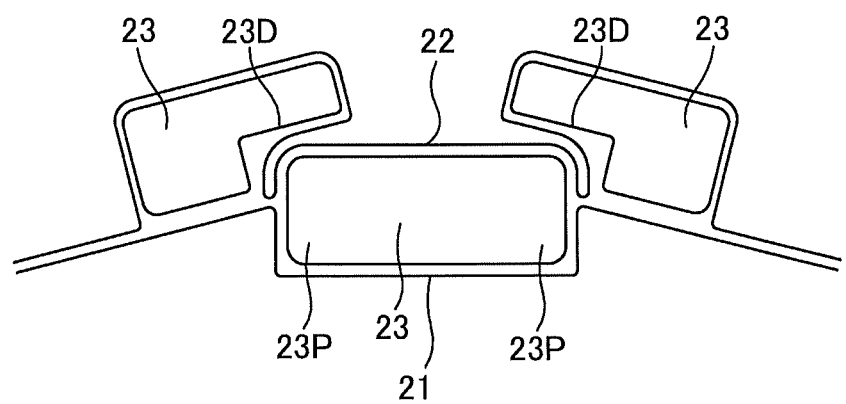

FIG.8
(a)
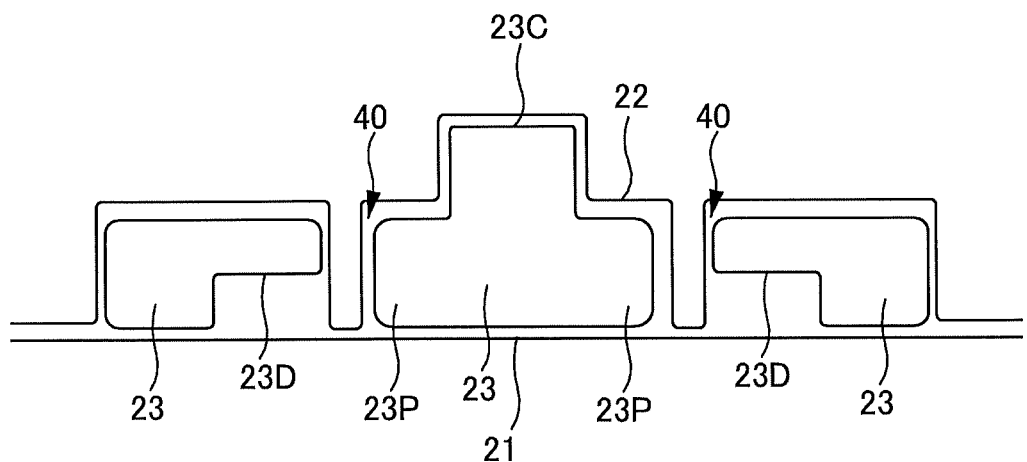
(b)
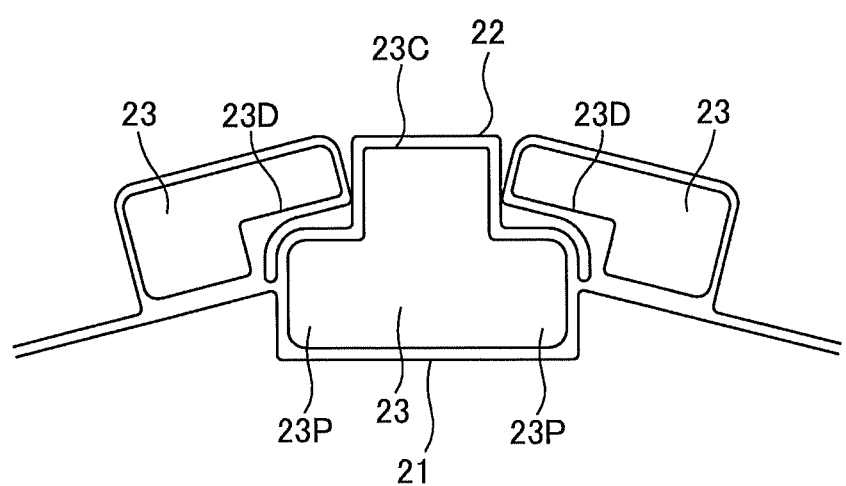

FIG.17
(a)
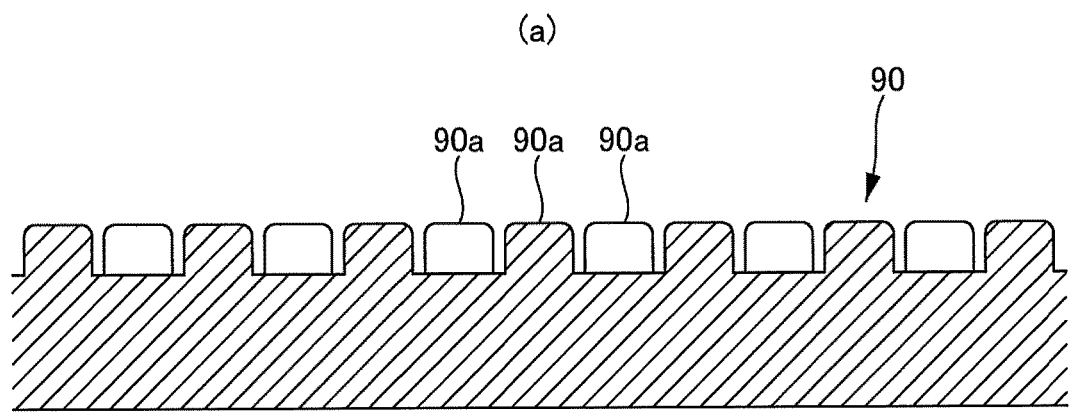
(b)
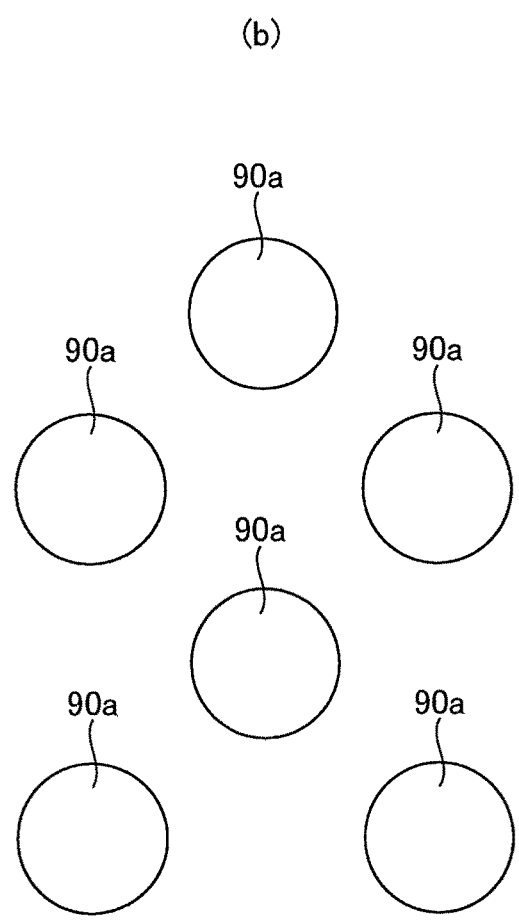

FIG.18
(a)
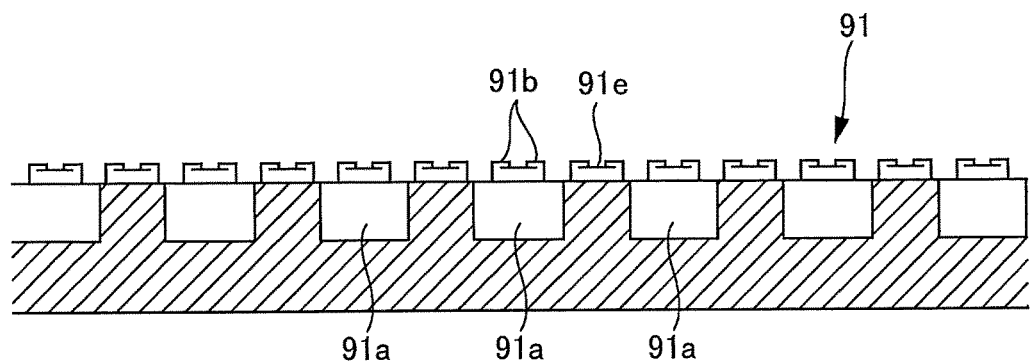
(b)
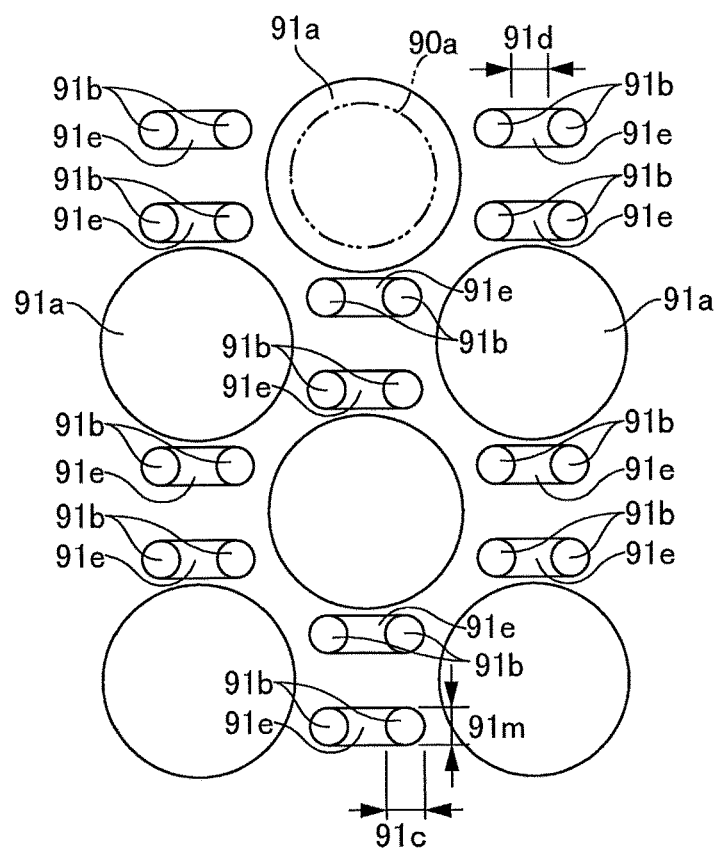

FIG.20
(a)
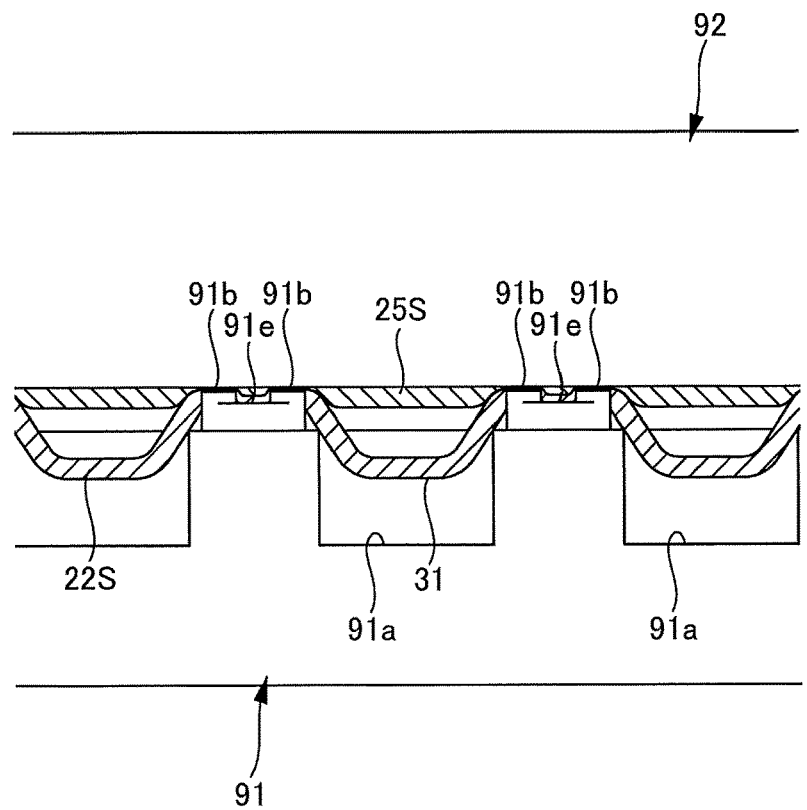
(b)
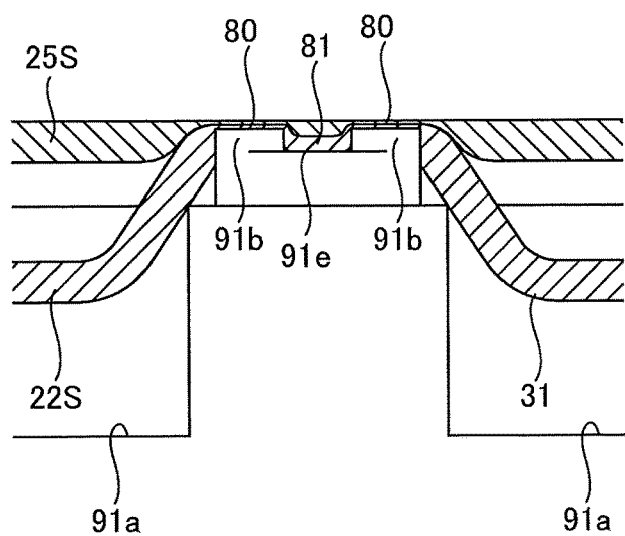

ABSORBENT ARTICLE HAVING A CAVITY PORTION AND A PROJECTION THAT FITS IN THE CAVITY PORTION

BACKGROUND OF THE INVENTION

1. Field of the Invention

The present invention relates to an absorbent article such as a disposal diaper or a sanitary napkin.

2. Description of the Related Art

When a wearer wears an absorbent article, a crotch portion of the absorbent article is sandwiched by both legs of the wearer, and is pressed to a certain extent in a width direction. A structure is known in which a plurality of slits each extending in a front and rear direction with a certain width is provided at a region of an absorbent body in the front and rear direction including the crotch portion in order to define a folded position to prevent the crotch portion of the absorbent article from being deformed into an undesired shape, to improve diffusibility in the front and rear direction from an expelling site and the like (see Patent Documents 1 and 2, for example).

PATENT DOCUMENTS

Patent Document 1

Japanese Laid-open Patent Publication No. 2015-039579

Patent Document 2

Japanese Laid-open Patent Publication No. 2012-157380

However, when such slits are provided, there is a problem that a slit forming region of the absorbent body is deformed largely by the movement of the legs to cause twisting or tearing, and the shape of the slits is easily changed.

SUMMARY OF THE INVENTION

Thus, the purpose of the present invention is to prevent twisting or tearing of a slit forming region of an absorbent body, and then prevent change of the shape of slits.

According to the embodiment, there is provided an absorbent article including a crotch portion; a front side portion and a rear side portion that are extended toward a front side and a rear side of the crotch portion, respectively; and an absorbent body provided at least at the crotch portion, wherein a pair of slits each extending in a front and rear direction with a predetermined width is formed in the absorbent body at a front and rear direction region at least at the crotch portion so as to section a first portion positioned at middle in a width direction, and a second portion and a third portion positioned at both sides of the first portion in the width direction, respectively, wherein the absorbent body includes projection portions projected toward both sides in the width direction at middle in the front and rear direction of the first portion, and wherein cavity portions in which the projection portions fit outwardly in the width direction are formed at a front and rear direction position corresponding to the projection portions in the second portion and the third portion, respectively.

As described above, according to the present invention, advantages such as twisting or tearing of a slit forming region of an absorbent body is prevented, and change of the shape of slits is prevented can be obtained.

BRIEF DESCRIPTION OF THE DRAWINGS

FIG. 4 is a cross-sectional view of FIG. 1;

FIG. 5 is a cross-sectional view schematically illustrating the pad type disposal diaper of an embodiment;

FIG. 8 is a cross-sectional view schematically illustrating another example of the pad type disposal diaper of the embodiment;

FIG. 17 is a view illustrating a pushing roller;

FIG. 18 is a view illustrating a concave roller;

FIG. 20 is an enlarged cross-sectional view illustrating a main part of a bonding step by the concave roller and the bonding roller.

DETAILED DESCRIPTION OF THE PREFERRED EMBODIMENTS

Hereinafter, embodiments of the invention are described in detail with reference to drawings. Among the following terms, a "crotch portion" means a portion corresponding to a crotch of a body when wearing, and may be a region from a center or its vicinity to a predetermined site at a front side of an article in a front and rear direction as the illustrated embodiment, or a predetermined region at the center of the article in the front and rear direction, depending on products. When a constricted portion whose width is narrow is provided at a middle of the article in the front and rear direction or at a middle of an absorbent body in the front and rear direction, the "crotch portion" means a predetermined region in the front and rear direction having its center at a minimum width region of one of or both of the constricted portions in the front and rear direction. Further, a "front side portion (ventral portion)" means a portion at a front side of the crotch portion, and a "rear side portion (dorsal portion)" means a portion at a rear side of the crotch portion.

In the following embodiments, a pad type disposal diaper is described as an example of an absorbent article.

FIG. 1 to FIG. 4 illustrate an example of a pad type disposal diaper 200 of the embodiment. The pad type disposal diaper 200 includes a crotch portion C2, and a front side portion F2 and a rear side portion B2 that are extending in front and rear of the crotch portion C2, respectively. The size of each portion may be properly defined, and for example, the total length of the article (the length in the front and rear direction) L may be approximately 350 to 700 mm, and the total width W1 may be approximately 130 to 400 mm (here, this is wider than the width of an absorbing surface of the diaper). In such a case, the length of the crotch portion C2 in the front and rear direction is approximately 10 to 150 mm, the length of the front side portion F2 in the front and rear direction is approximately 50 to 350 mm, and the length of the rear side portion B2 in the front and rear direction is approximately 50 to 350 mm. Further, the width W3 of the crotch portion C2, for adults, may be greater than or equal to 150 cm, and particularly, may be approximately 200 to 260 cm.

Figure 3:
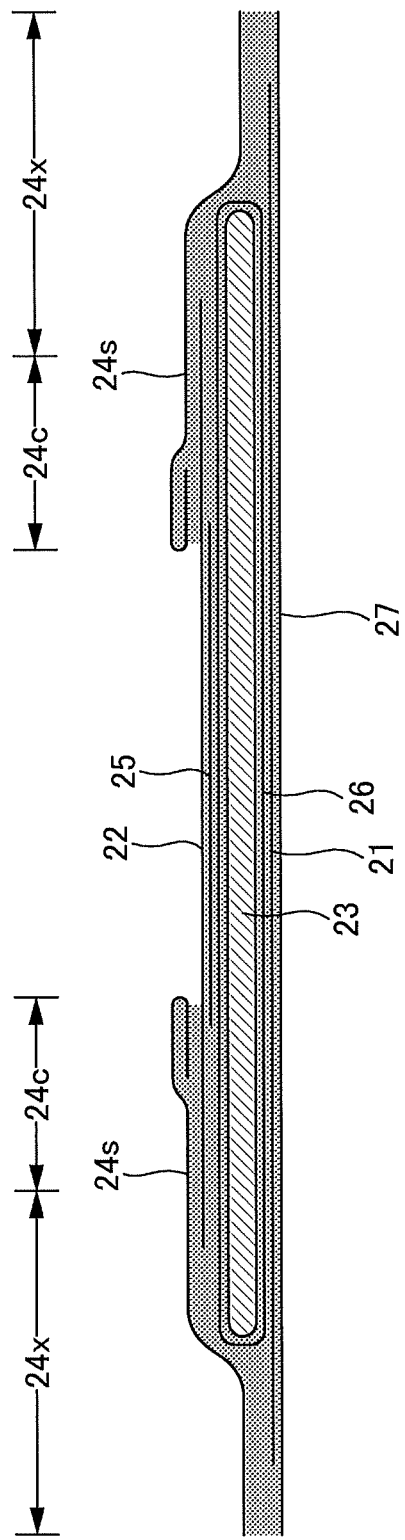
FIG. 3 is a cross-sectional view taken along Y-Y of FIG. 1.

As illustrated in FIG. 3, the pad type disposal diaper 200 has a basic structure in which an absorbent body 23 is disposed between an inner surface of a liquid impermeable sheet 21, on an outer surface of which an exterior sheet 27 is stacked, and a liquid permeable topsheet 22.

The liquid impermeable sheet 21 is provided at a back side of the absorbent body 23 so as to slightly protrude from a periphery of the absorbent body 23. As the liquid impermeable sheet 21, in addition to a polyethylene film or the like, a sheet having moisture permeability without losing a water shielding property may be used in order to prevent sweating. For such a water shielding and moisture permeability sheet, for example, a microporous sheet may be used that is obtained by forming a sheet by melting and kneading inorganic filler in olefin resin such as polyethylene or polypropylene and then extruding the sheet in one axial direction or two axial directions.

Further, the outer surface of the liquid impermeable sheet 21 is covered by the exterior sheet 27 made of a non-woven-fabric. The exterior sheet 27 is outwardly protruded from a periphery of the back sheet 21 with a predetermined protruding width. As the exterior sheet 27, various non-woven-fabrics may be used. As a material fiber for constituting the non-woven fabric, a synthetic fiber including an olefin series such as polyethylene or polypropylene, a polyester series, a polyamide series and the like, a regenerated fiber such as rayon or cupra (cuprammonium rayon), or a natural fiber such as cotton may be used.

A top side of the absorbent body 23 is covered by the liquid permeable topsheet 22. Although a part of the absorbent body 23 is protruded from side edges of the topsheet 22 in the illustrated embodiment, the width of the topsheet 22 may be extended such that side edges of the absorbent body 23 are not protruded. As the topsheet 22, a perforated or imperforate non-woven fabric or a porous plastic sheet may be used. As a material fiber for constituting the non-woven fabric, a synthetic fiber including an olefin series such as polyethylene or polypropylene, a polyester series, a polyamide series and the like, a regenerated fiber such as rayon or cupra (cuprammonium rayon), or a natural fiber such as cotton may be used.

It is preferable that an intermediate sheet 25 is disposed between the topsheet 22 and the absorbent body 23. The intermediate sheet 25 is provided to prevent flow back of urine absorbed in the absorbent body 23, and it is preferable that a material with a low water holding capacity and high permeability such as various non-woven-fabrics or mesh films are used, for example. When it is assumed that a front end of the topsheet 22 is 0%, and a rear end of the topsheet 22 is 100%, it is preferable that a front end of the intermediate sheet 25 is positioned within a range of 0 to 11%, and a rear end of the intermediate sheet 25 is positioned within a range of 92 to 100%. Further, it is preferable that the width W4 of the intermediate sheet 25 is approximately 50 to 100% of the minimum width W5 of a constricted portion 23n of the absorbent body 23, which will be described later.

At both end portions of the pad type disposal diaper 200 in the front and rear direction, the exterior sheet 27 and the liquid permeable topsheet 22 are extended further than both end sides of the absorbent body 23 at the front and rear ends to be adhered with each other, and end flap portions EF at which the absorbent body 23 does not exist are formed. The exterior sheet 27 is outwardly extended from side edges of the absorbent body 23 at both side portions of the pad type disposal diaper 200. Laterally outer portions 24x of gather sheets 24s that form standing gathers 24, respectively are adhered at an inner surface of the exterior sheet 27 from the extended portions to side portions of the topsheet 22 at the entirety in the front and rear direction to form side flaps SF at which the absorbent body 23 does not exist. These laminated portions are illustrated by oblique lines in FIG. 1, and may be formed by a hot-melt adhesive, a heat seal or ultrasonic sealing. When the exterior sheet 27 is not provided, the liquid impermeable sheet 21 may be extended to the side flaps SF instead of the exterior sheet 27 to form the outer surfaces of the side flaps SF.

As a material of the gather sheets 24s, a plastic sheet or a melt blown non-woven-fabric may be used, but preferably, a non-woven-fabric to which a water-repellent treatment is performed by silicon is used for improving feeling to skin.

Laterally center side portions 24c of the gather sheets 24s are extended over the topsheet 22, and elongated elastic members 24G are fixed at end portions at a center side in the width direction along the front and rear direction under an extended state by a hot-melt adhesive or the like. As the elongated elastic member 24G, a material that is normally used may be used such as a styrene series rubber, an olefin series rubber, a urethane series rubber, an ester series rubber, polyurethane, polyethylene, polystyrene, styrene-butadiene, silicon, polyester or the like that is formed into a threadlike form, a string-like form, a strip-like form or the like.

Figure 1:
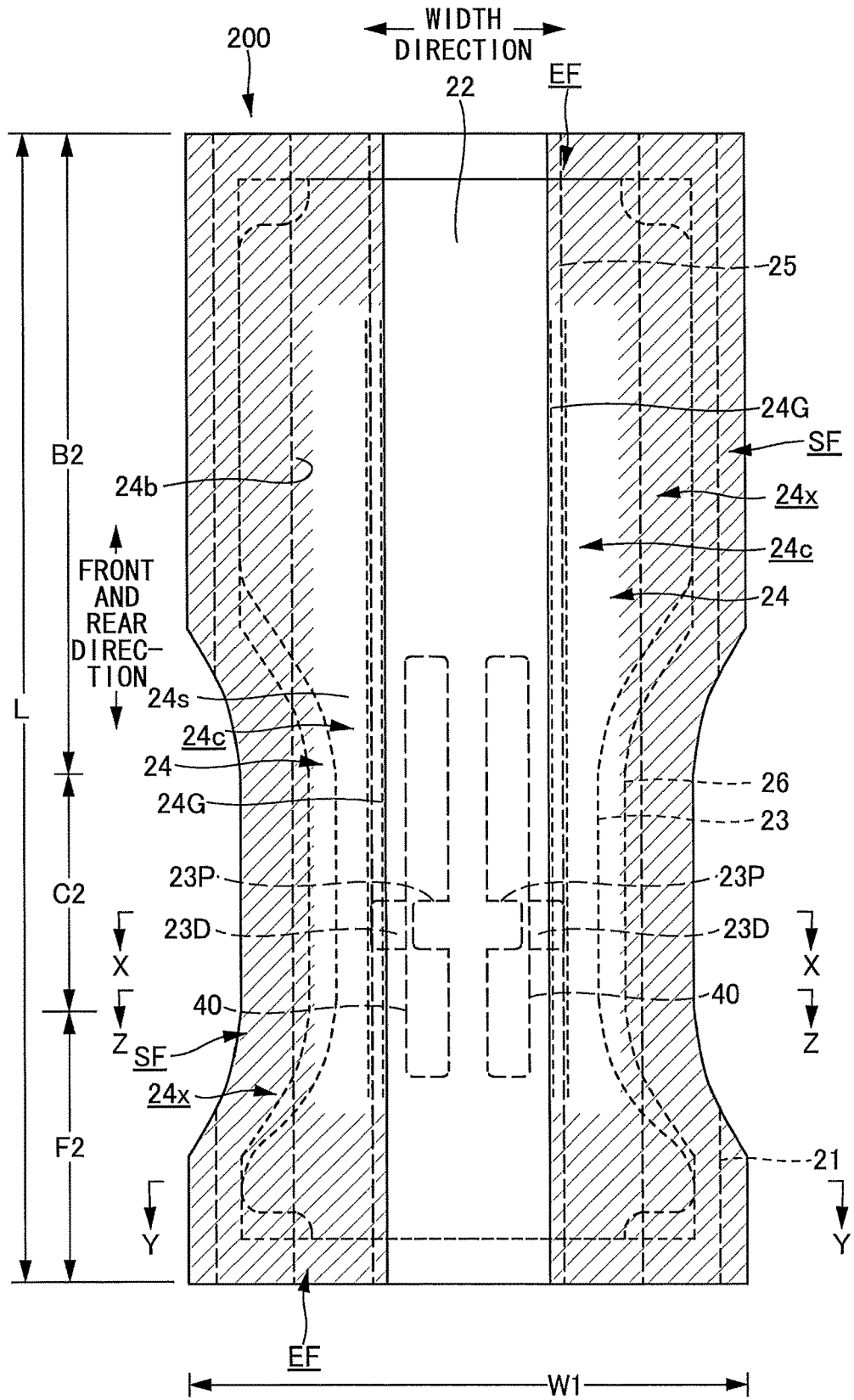
FIG. 1 is a plan view illustrating an inner surface side of a pad type disposal diaper at a spread state.

Further, the laterally outer portions 24x of the both of the gather sheets 24s are fixed by being adhered to an inner surface of the article (in the illustrated embodiment, the top surface of the topsheet 22 and the inner surface of the exterior sheet 27) over the entirety in the front and rear direction. Further, the laterally center portions 24c of the both of the gather sheets 24s are fixed by being adhered to the inner surface of the article (in the illustrated embodiment, the top surface of the topsheet 22) at both end portions in the front and rear direction, but are not fixed to the inner surface of the article (in the illustrated embodiment, the top surface of the topsheet 22) at a region between the both end portions in the front and rear direction. As illustrated in FIG. 1, this non-fixed portion functions as a leakage preventing wall that flexibly stands with respect to the inner surface of the article (in the illustrated embodiment, the top surface of the topsheet 22), and its standing base edge 24b is positioned on an interface of the laterally outer fixed portion 24x and the laterally center portion 24c of the gather sheet 24s.

As the absorbent body 23, a fiber stacking body of pulp fiber, aggregation of a filament such as cellulose acetate, or a non-woven-fabric may be used as a base, and a super absorbent polymer in a particle form or the like may be mixed, adhered or the like in accordance with necessity. The absorbent body 23 may be wrapped by a packaging sheet 26 such as a crepe paper, if necessary such as when the super absorbent polymer particles are mixed. Further, the shape of the absorbent body 23 may be formed into a proper shape such as a strip shape in which the width at a front side portion is relatively narrower than that at a rear side portion, or alternatively, a rectangular shape, a trapezoid shape or the like.

The fabric weight per unit area of the absorbent body 23 and the weight per unit area of the super absorbent polymer may be properly determined, and it is preferable that the fabric weight per unit area is approximately 100 to 600 g/m², and the weight per unit area of the absorbent polymer is approximately 0 to 400 g/m².

The absorbent body 23 is extended from the front side portion F2 toward the rear side portion B2, and in the illustrated embodiment, a predetermined portion including the crotch portion C2 at a middle in the front and rear direction is formed as the constricted portion 23n whose width is narrow. It is preferable that the minimum width W5 of the constricted portion 23n is approximately 50 to 65% of the width W2 of non-constricted portions positioned at front and rear of the constricted portion 23n, respectively. Further, when it is assumed that a front end of the article is 0% and a rear end of the article is 100%, it is preferable that a front end of the constricted portion 23n is positioned within a range of 10 to 25%. Further, it is preferable that a rear end of the constricted portion 23n is positioned within a range of 40 to 65%. Further, it is preferable that a site of the constricted portion 23n whose width becomes the minimum width W5 (minimum width region) is positioned within a range 25 to 30%.

In the pad type disposal diaper 200 of the embodiment, a pair of slits 40 each extending in the front and rear direction is formed in the absorbent body 23. The pair of slits 40 is formed at a region corresponding to at least the crotch portion C2 in the front and rear direction in the absorbent body 23 to section a first portion 11 positioned at middle in the width direction and a second portion 12 and a third portion 12 positioned at both sides thereof in the width direction. Further, the absorbent body 23 includes projection portions 23P projected toward both sides in the width direction in the pair of slits 40, respectively, at middle of the first portion 11 in the front and rear direction. Further, the absorbent body 23 includes cavity portions 23D in which the projection portions 23P fit outwardly in the width direction, respectively, at a position corresponding to the projection portions 23P in the front and rear direction in the second portion 12 and the third portion 12, respectively.

Although the first portion 11 and the second portion 12 and the third portion 12 are integrally formed via portions at front and rear thereof in the absorbent body 23 of the illustrated embodiment, in another embodiment, the second portion 12 and the third portion 12 may be formed separately from the first portion 11. Further, it is preferable that sheet(s) positioned above the slits 40 fall in each of the slits 40 in the illustrated embodiment, the sheet(s) may extend along a surface without falling in the slits 40. Although the sheet(s) positioned above the slits 40 are the topsheet 22, the intermediate sheet 25 and a top side portion of the packaging sheet 26 in the illustrated embodiment, the sheets other than the topsheet 22 may not be included.

As long as the slits 40 are formed at the crotch portion C2, the length 40L in the front and rear direction is not particularly limited, and thus, the slits 40 may be provided over the entirety of the absorbent body 23 in the front and rear direction. However, it is preferable that the slits 40 are formed to extend from an end portion of the front side portion F2 at a crotch side to an end portion of the rear side portion B2 at a crotch side, as the illustrated embodiment.

Figure 9:
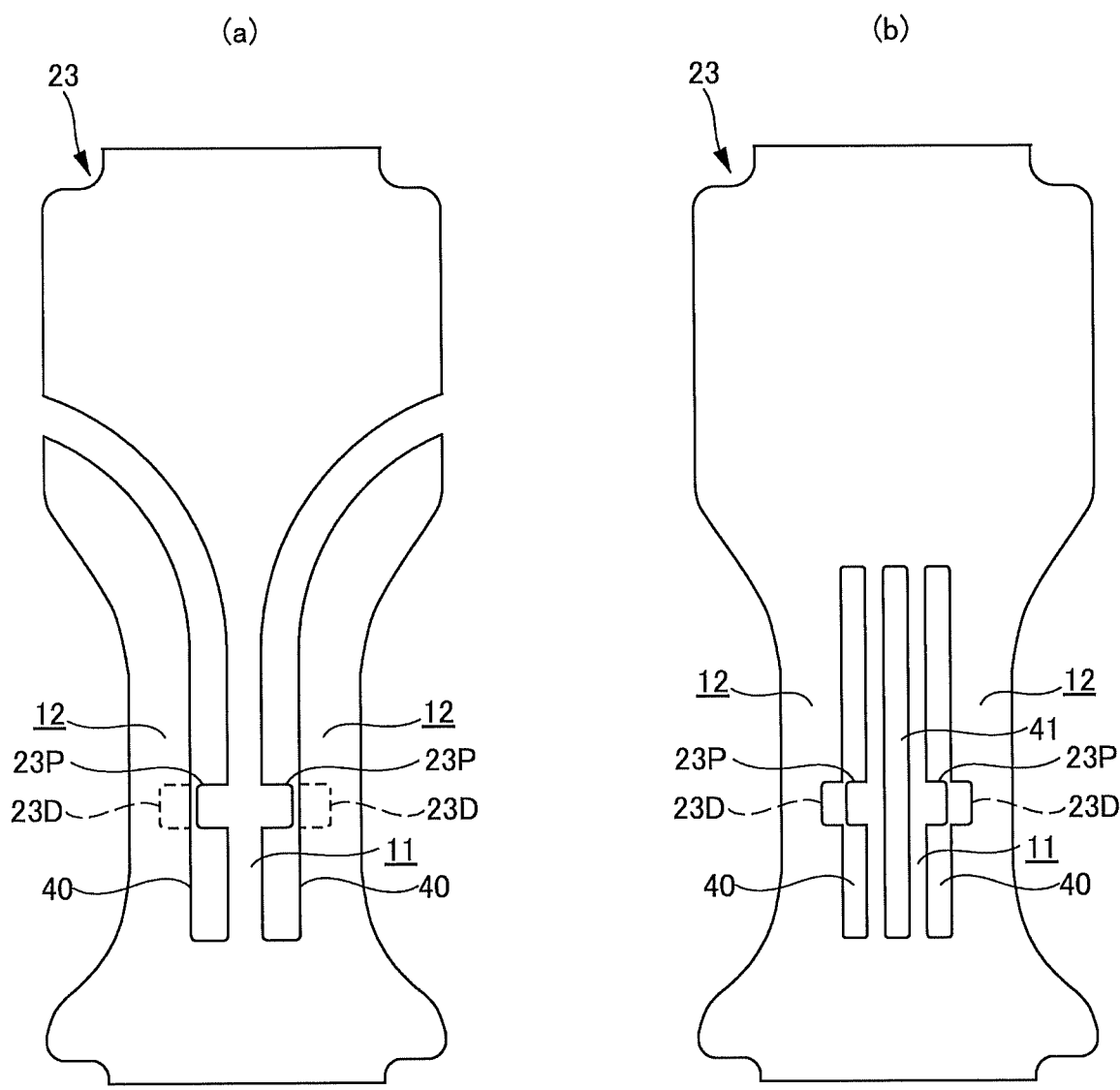
FIG. 9 is a plan view illustrating another example of the absorbent body of the embodiment.

FIG. 9-(a) and FIG. 9-(b) are plan views illustrating another example of the absorbent body 23 of the embodiment. As illustrated in FIG. 9-(a), a rear side portion of the slit 40 may be bent outwardly in the width direction (a front side portion may be similarly bent). As illustrated in FIG. 9-(b), another slit 41 may be provided at a center in the width direction. More specifically, when it is assumed that a front end of the disposal diaper 200 is 0%, and a rear end of the disposal diaper 200 is 100%, it is preferable that a front end of the slit 40 is positioned within a range of 15 to 30%, and a rear end of the slit 40 is positioned within a range of 40 to 70%.

As long as the slits 40 are laterally symmetry, positions of the slits 40 in the width direction may be properly determined. Normally, it is preferable that a distance 40D between the bilateral slits 40 is approximately 10 to 30% of the minimum width W5 of the constricted portion 23n of the absorbent body 23.

As long as facing side walls are apart from each other, the width 40W of the slit 40 is not particularly limited. Normally, it is preferable that the width 40W is approximately 200 to 520% of the thickness of a center portion including the absorbent body 23 in the width direction, and specifically, for an adult product, may be approximately 5 to 32 mm.

The sizes of the projection portions 23P and the cavity portions 23D of the absorbent body 23 may be properly determined. As an example, it is preferable that the length PW of the projection portion 23P in the width direction is approximately 50 to 100% of the width 40W of the slit 40. Further, it is preferable that the length PL of the projection portion 23P in the front and rear direction is approximately 10 to 30% of the length 40L of the slit 40 in the front and rear direction. It is preferable that the length DW of the cavity portion 23D in the width direction is approximately 50 to 100% of the length PW of the projection portion 23P in the width direction. Further, it is preferable that the length DL of the cavity portion 23D in the front and rear direction is approximately 100 to 120% of the length PL of the projection portion 23P in the front and rear direction.

FIG. 5-(a) is a cross-sectional view schematically illustrating a spread state of the pad type disposal diaper 200 of the embodiment. FIG. 5-(b) is a cross-sectional view schematically illustrating a worn state of the pad type disposal diaper 200 of the embodiment. In the pad type disposal diaper 200 having the above described configuration, as can be understood from the comparison between the spread state illustrated in FIG. 5-(a) and the worn state illustrated in FIG. 5-(b), when the crotch portion C2 is sandwiched by both legs of a wearer, pressed to a certain extent in the width direction, and both sides of the slits 40 are close to each other, the projection portions 23P of the first portion 11 fit the cavity portion 23D of the second portion 12 and the cavity portion 23D of the third portion 12, respectively (including an embodiment in which the projection portions 23P loosely fit). Thus, integration of the first portion 11 (a portion between the slits 40) with the second portion 12 and the third portion 12 (laterally outer portions of the slits 40) is increased, and a region of the absorbent body 23 where the slits 40 are formed is hardly deformed by movement of the legs, twisting or tearing hardly occurs and the shape of the slits 40 hardly changes.

Figure 2:
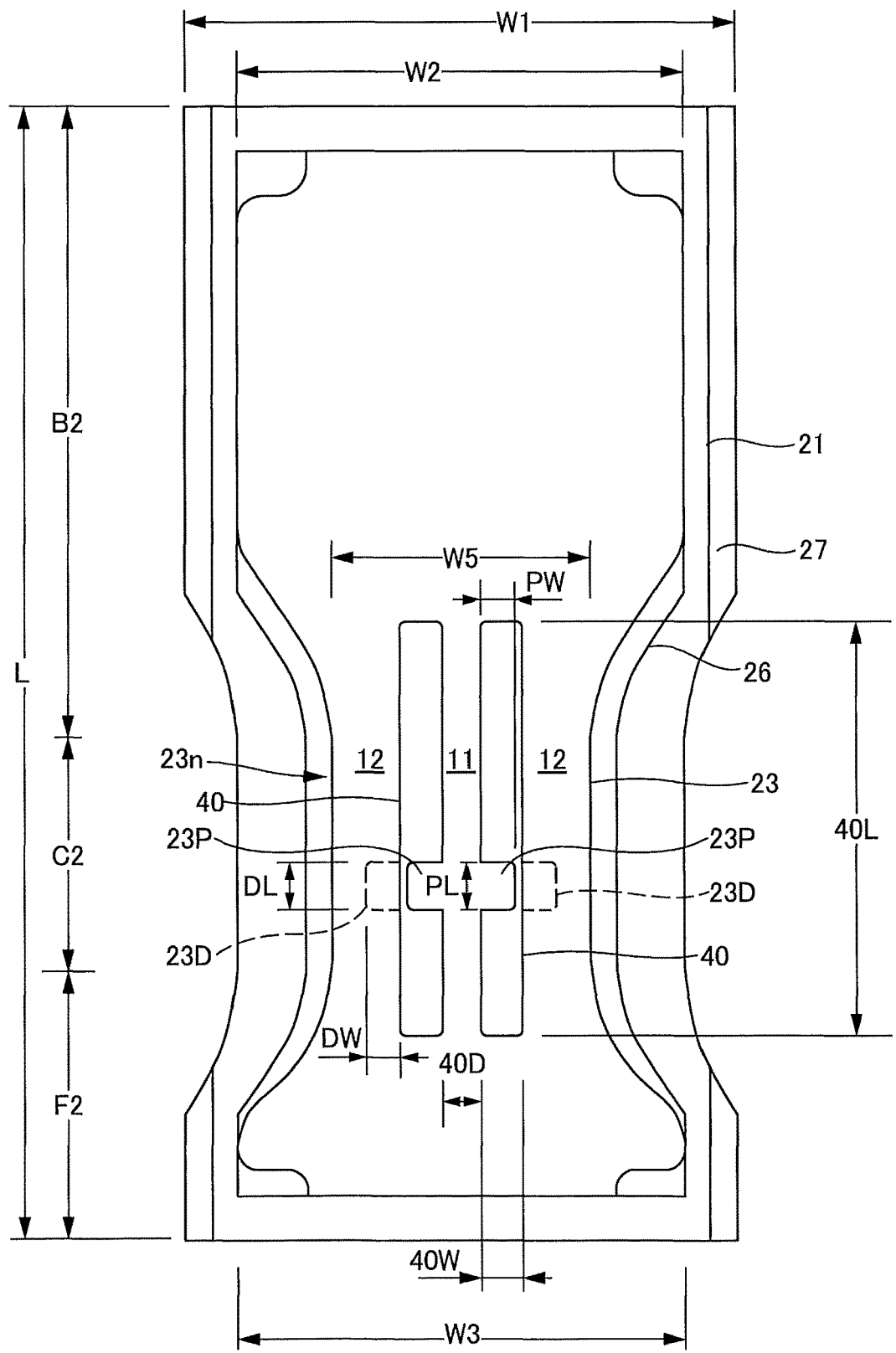
FIG. 2 is a plan view illustrating only a main portion.

The shape of the cavity portion 23D in each of the second portion 12 and the third portion 12 may be properly determined, and for example, as illustrated in FIG. 2 and FIG. 4-(a), the cavity portion 23D may not be formed over the entirety in the thickness direction of the absorbent body 23, but may be formed as a groove-like portion that extends from a side edge of the first portion 11 outwardly in the width direction only formed at a back surface side of each of the second portion 12 and the third portion 12. By forming the cavity portion 23D as such a groove-like portion, as illustrated in FIG. 5-(b), the projection portions 23P of the first portion 11 can fit the cavity portion 23D of the second portion 12 and the cavity portion 23D of the third portion 12 while the second portion 12 and the third portion 12 are positioned above the first portion 11. At this time, as a space is formed between the second portion 12 and the third portion 12, a groove, for which the second portion 12 and the third portion 12 are side portions and the first portion 11 is a bottom portion, is formed to extend in the front and rear direction. Further, at this time, even when the second portion 12 and the third portion 12 contact with each other, a small groove that extends along the front and rear direction is formed at their interface. Thus, even when the crotch portion C2 is pressed in the width direction and the slits 40 are collapsed, lowering of diffusibility in the front and rear direction can be suppressed.

Alternatively, for example, as illustrated in FIG. 9-(b), the cavity portion 23D in each of the second portion 12 and the third portion 12 may be formed over the entirety of the absorbent body 23 in the thickness direction. In other words, portions of the second portion 12 and the third portion 12 corresponding to the projection portions 23P, respectively, are formed to concave outwardly in the width direction over the entirety in the thickness direction.

As long as at least a front end portion of the projection portion 23P can fit, the size of the cavity portion 23D may be properly determined. However, in order to from the groove whose side portions are the second portion 12 and the third portion 12 and whose bottom portion is the first portion 11 at the worn state as described above, it is preferable that a total of the length of the groove-like portion of the second portion 12 in the width direction and the length of the groove-like portion of the third portion 12 in the width direction (in other words, in the illustrated embodiment, two times of the length DW of the cavity portion 23D in the width direction) is shorter than the width of a portion of the first portion 11 where the projection portions 23P are provided.

Figure 6:
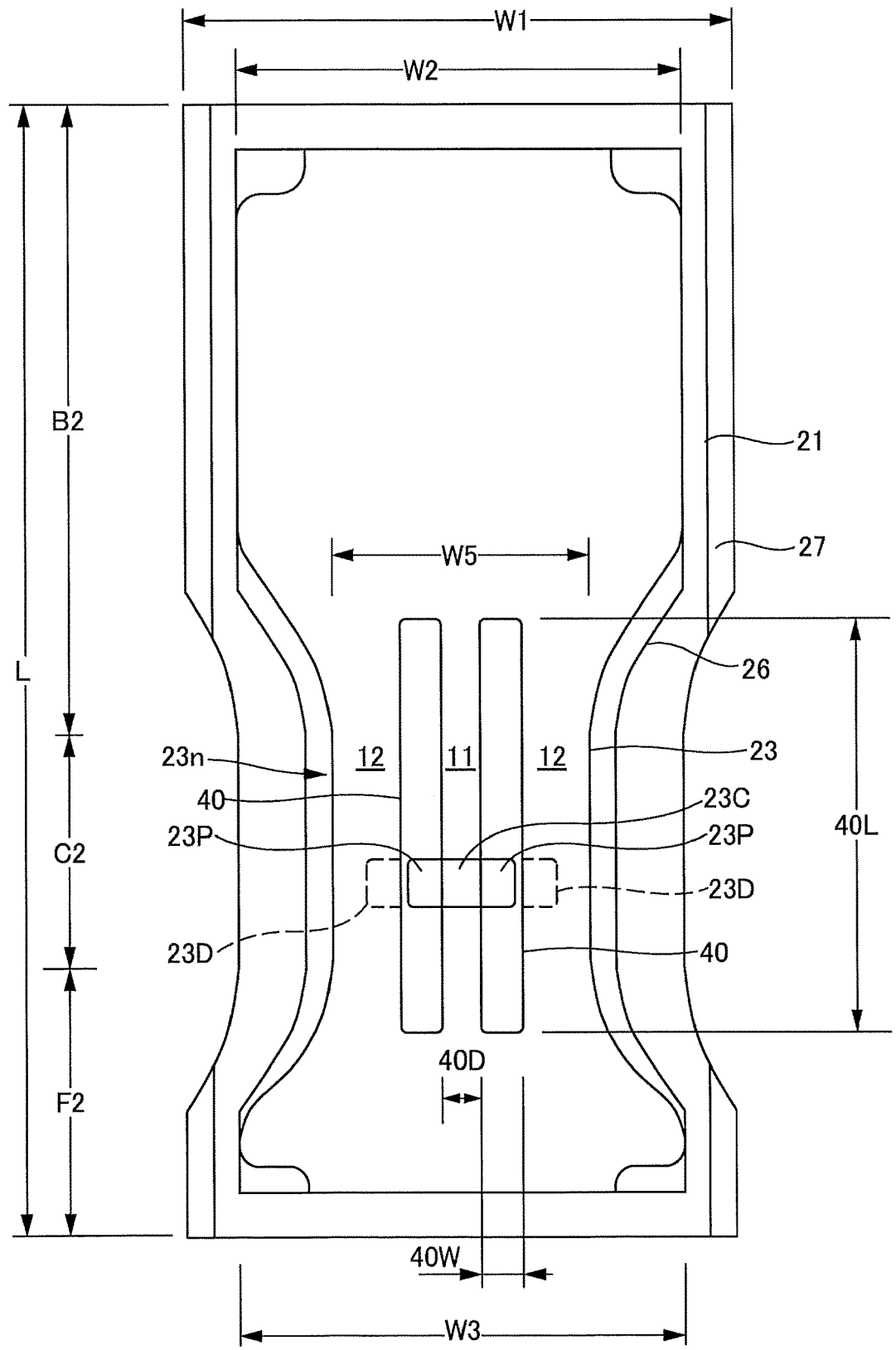
FIG. 6 is a plan view illustrating only a main portion of another example.
Figure 7:
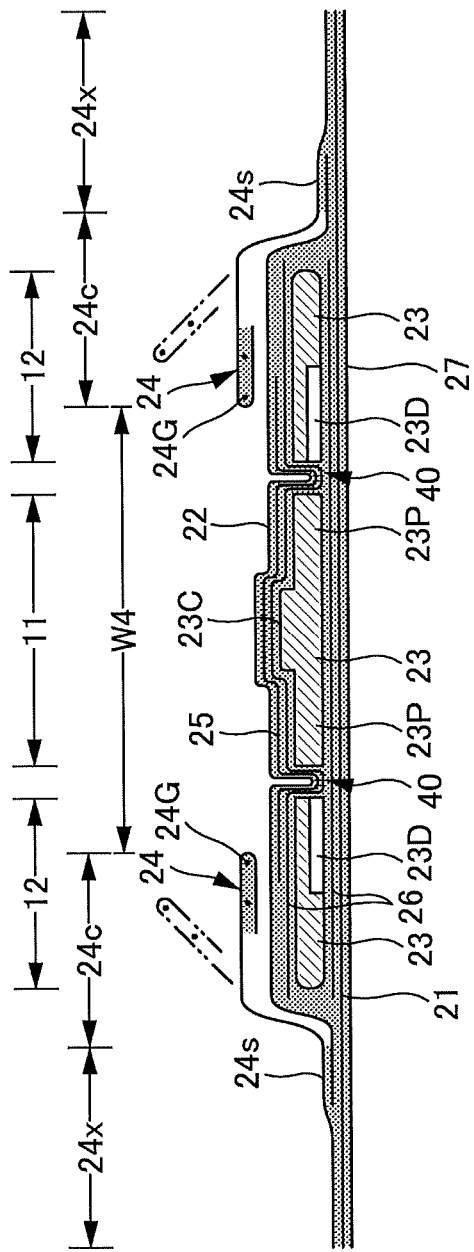
FIG. 7 is a cross-sectional view of the embodiment of another example taken along Z-Z of FIG. 1.

FIG. 6 to FIG. 8 illustrate another example of the pad type disposal diaper 200 of the embodiment. In this example, as illustrated in FIG. 6 to FIG. 8, a portion between the projection portions 23P of the first portion 11 is formed as a movement stop portion 23C in which at least an intermediate portion in the width direction protrudes toward atop side with respect to portions at both sides in the width direction. By providing such a movement stop portion 23C, when the projection portions 23P of the first portion 11 respectively fit the cavity portion 23D of the second portion 12 and the cavity portion 23D of the third portion 12 while the second portion 12 and the third portion 12 are positioned above the first portion 11, the second portion 12 and the third portion 12 knock against the movement stop portion 23C without moving opposite sides from the movement stop portion 23C. In other words, the second portion 12 and the third portion 12 are prevented from being positioned too close to a center in the width direction after being positioned above the first portion 11.

The size of the movement stop portion 23C may be properly determined, and the length of the movement stop portion 23C in the width direction may be approximately 20 to 50% of the length of the portion between the projection portions 23P in the width direction. The length of the movement stop portion 23C in the front and rear direction is approximately 80 to 120% of the length of the projection portion 23P in the front and rear direction.

Next, the topsheet 22 and a bonding portion of the topsheet 22 and the intermediate sheet 25 are described. As illustrated in FIG. 10 to FIG. 13-(c), the topsheet 22 may have a structure in which multiple convex portions 31 are aligned with a space in the width direction and in the front and rear direction, respectively, by extruding from a back side to a top side by embossing. Here, the numeral "32" indicates a portion between the adjacent convex portions 31.

In this embodiment, at least regions corresponding to both side portions of the first portion 11 and regions that are adjacent to them at outsides in the width direction of a surface of the pad type disposal diaper 200 (in other words, a surface of the topsheet 22) may be formed as a concavo-convex surface in which multiple convex portions (convex portions 31) are aligned with a space therebetween in the width direction and in the front and rear direction. Then, the convex portions of each of the concavo-convex surfaces may be formed such that the concavo-convex surface at the regions corresponding to the both side portions of the first portion 11 and the concavo-convex surface at the regions that are adjacent to them at outsides in the width direction engage with each other. When the second portion 12 and the third portion 12 are positioned above the first portion 11, as illustrated in FIG. 5-(b) and FIG. 8-(b), the surfaces of the regions that are adjacent to the regions corresponding to the both side portions of the first portion 11 at outsides in the width direction, while being turned over, contact the surfaces of the regions corresponding to the both side portions of the first portion 11. Thus, if the facing surfaces that contact are formed as the concavo-convex surfaces capable of engaging with each other, integration between the second portion 12 and the third portion 12 and the first portion 11 under a state that the second portion 12 and the third portion 12 are positioned above the first portion 11 is furthermore improved.

As long as the concavo-convex surfaces can engage with each other, in other words, as long as an apex of each of the convex portions at one of the facing surfaces can get into a space between the adjacent convex portions of the other of the facing surfaces, the size, the shape, the arrangement and the structure of the convex portions are not particularly limited, and the known size, the shape, the arrangement and the structure may be appropriately adopted. The following is an example.

Figure 10:
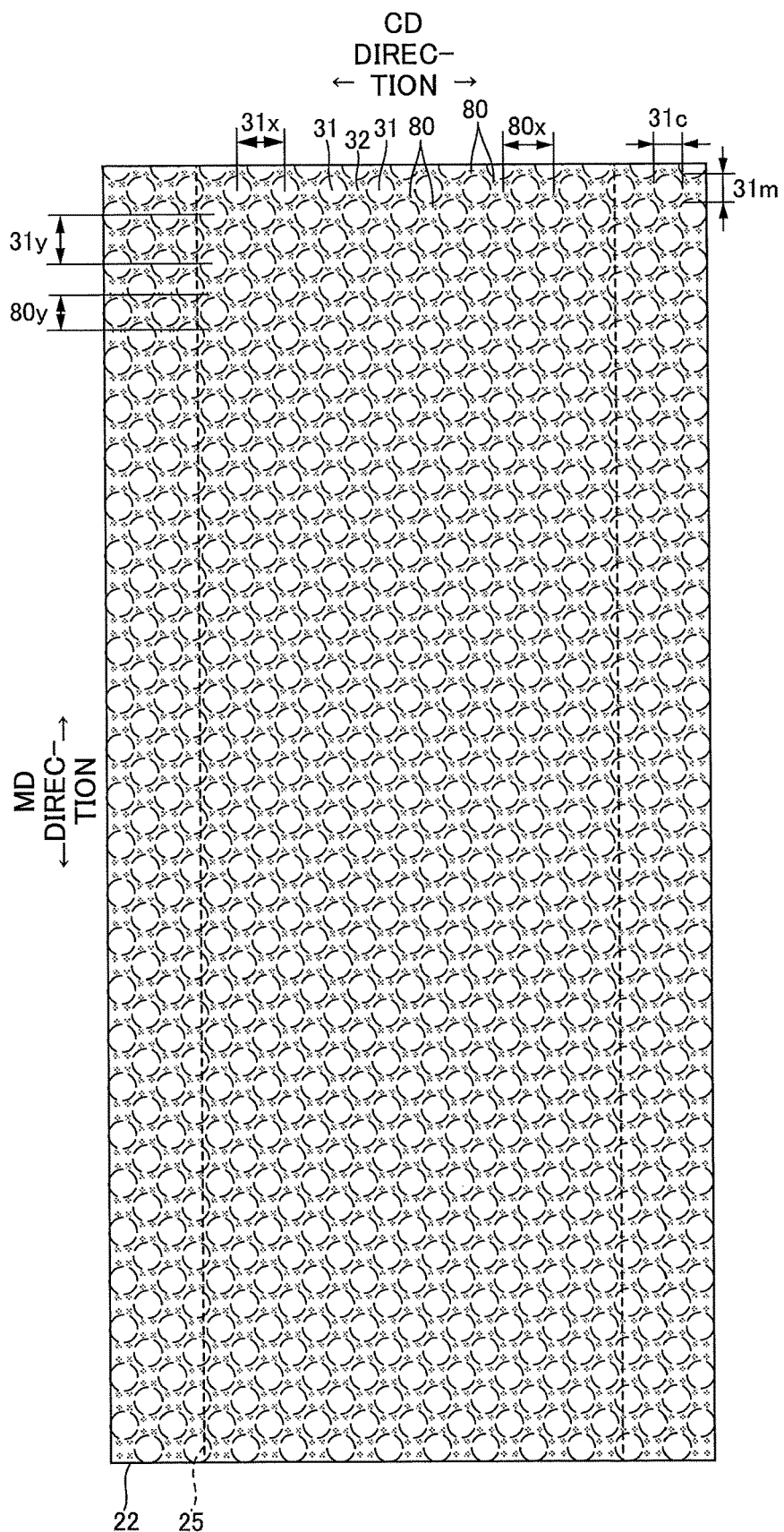
FIG. 10 is a plan view of a topsheet and an intermediate sheet.
Figure 11:
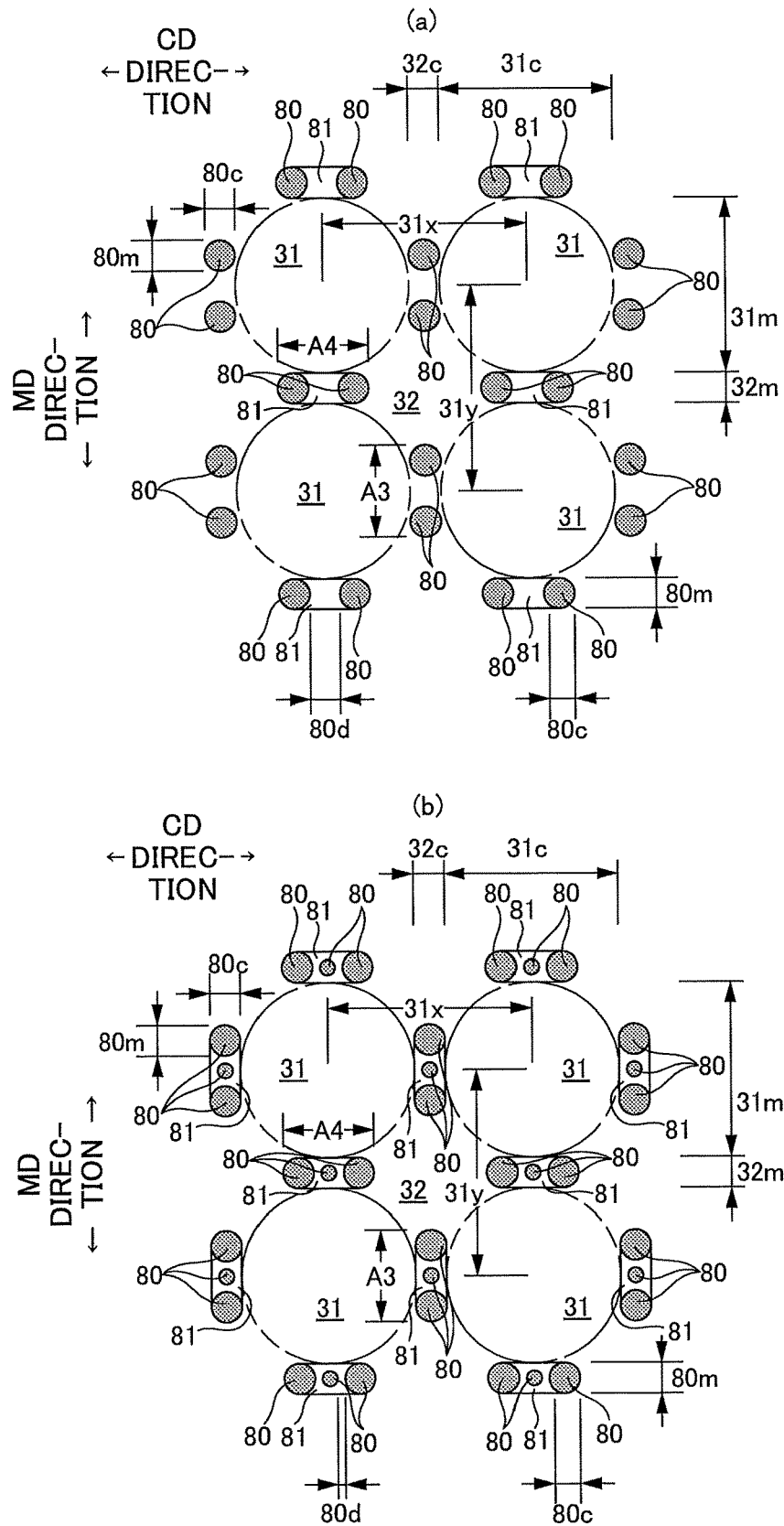
FIG. 11 is an enlarged plan view illustrating an example of a bonding pattern of a topsheet bonding portion.
Figure 12:
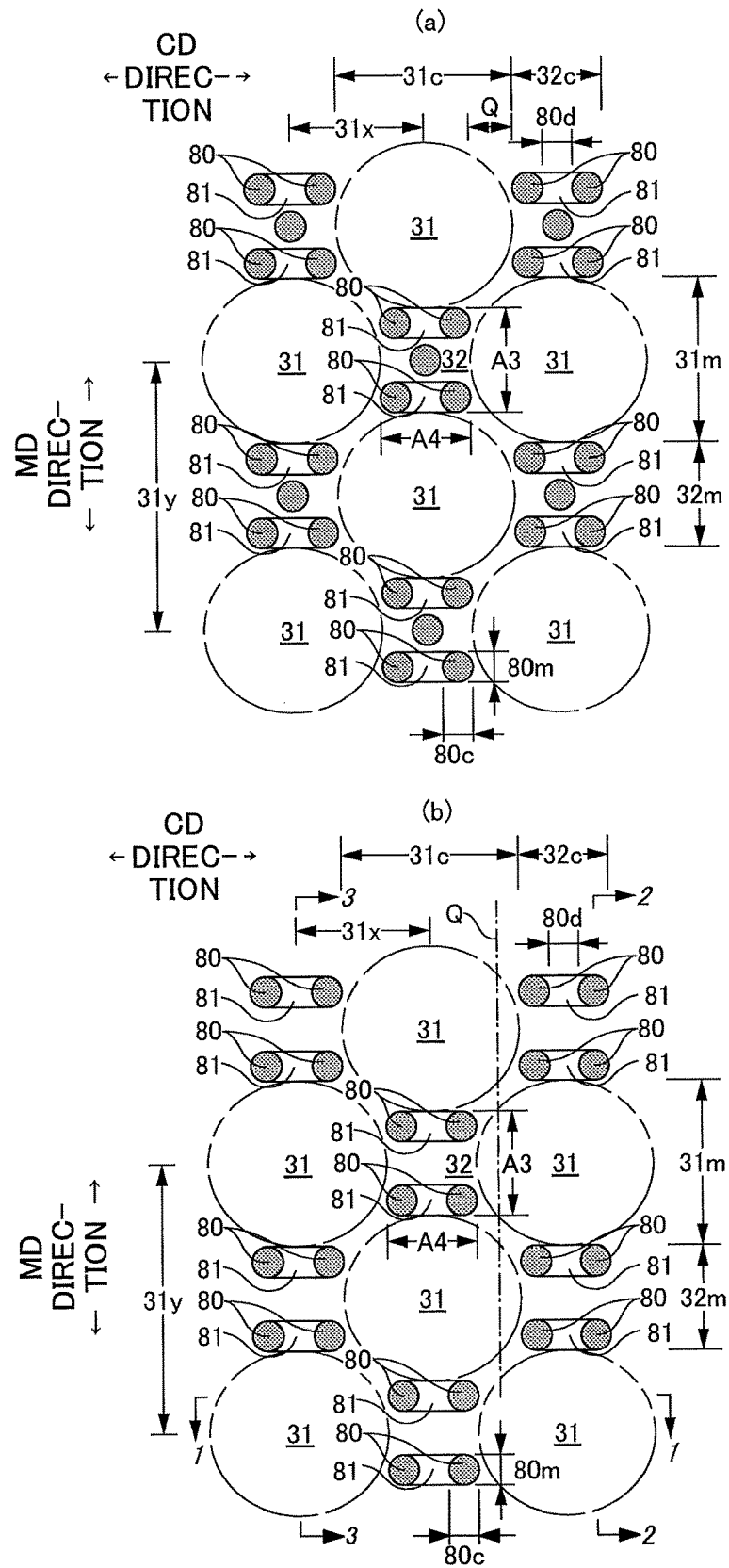
FIG. 12 is an enlarged plan view illustrating an example of the bonding pattern of the topsheet bonding portion.

This arrangement format may be selectable, such as in a matrix form as illustrated in FIG. 11-(a) and FIG. 11-(b), or in a staggered form (an arrangement in which the convex portions are alternately provided in adjacent lines) as illustrated in FIG. 10, FIG. 12-(a) and FIG. 12-(b). Further, although an embodiment in which the convex portions 31 are provided over almost the entirety of the topsheet 22 is assumed in the illustrated embodiment, as described above, the convex portions 31 may be partially provided as long as being provided at least at the regions corresponding to the both side portions of the first portion 11 and the regions that are adjacent to them at outsides in the width direction. For example, the convex portions 31 may be provided at almost the entirety of the region where the topsheet 22 and the intermediate sheet 25 overlap. FIG. 12-(b) is an enlarged view of a structure illustrated in FIG. 10. Further, FIG. 11-(a), FIG. 11-(b) and FIG. 12-(a) illustrate the other examples.

The size and the like of the convex portion 31 may be properly determined, and as illustrated in FIG. 10 to FIG. 12-(b), it is preferable that the size 31m of the convex portion 31 in a MD (machine direction) direction is less than or equal to a distance 80y between centers of a topsheet bonding portion 80 (described later) positioned at one side of the convex portion 31 and a topsheet bonding portion 80 positioned at the other side of the convex portion 31 in the MD direction, and it is preferable that its lower limit is approximately 0.9 times, and normally, approximately 2.7 to 9 mm. Similarly, it is preferable that the size 31c of the convex portion 31 in a CD (cross direction) direction is less than or equal to a distance 80x between centers of a topsheet bonding portion 80 positioned at one side of the convex portion 31 and a topsheet bonding portion 80 positioned at the other side of the convex portion 31 in the CD direction, and it is preferable that its lower limit is approximately 0.9 times, and normally, approximately 2.7 to 9 mm. Further, normally, it is preferable that the height 31z of the convex portion 31 is approximately 0.8 to 2 mm. The numeral "32m" indicates a space between the convex portions 31 aligned in the MD direction, and "32c" indicates a space between the convex portions 31 aligned in the CD direction.

Here, the "MD direction" and the "CD direction" of a product mean a "MD direction" and a "CD direction" of a processing plant of the convex portion 31, and one of them becomes the front and rear direction and the other of them becomes the width direction. Then, the MD direction of the product is a direction of a fiber orientation of the non-woven-fabric of the topsheet 22. The fiber orientation is a direction in which the fibers of the non-woven-fabric extend, and may be determined by, for example, a measurement method according to TAPPI STD T481, fiber orientation testing by zero-span tensile strength, or a simple measurement method by which the fiber orientation is decided from the tensile strength ratio in the front and rear direction and in the width direction. In the illustrated embodiment, similar to the almost all of absorbent article products, the front and rear direction is the MD direction and the width direction is the CD direction.

Although the distance between the convex portions 31 may be properly determined, for the case of the matrix form as illustrated in FIG. 11-(a) and FIG. 11-(b), it is preferable that a distance 31x in the CD direction between centers of the convex portions 31 of the MD direction lines that are adjacent in the CD direction is approximately 3 to 10 mm, and a distance 31y in the MD direction between centers of the convex portions 31 of the CD direction lines that are adjacent in the MD direction is approximately 3 to 10 mm. Further, for the case of the staggered form as illustrated in FIG. 10, FIG. 12-(a) and FIG. 12-(b), it is preferable that a distance 31x in the CD direction between centers of the convex portions 31 of the MD direction lines that are adjacent in the CD direction is approximately 3 to 10 mm, and a distance 31y in the MD direction between centers of the convex portions 31 of the CD direction lines that are adjacent in the MD direction is approximately 3 to 10 mm.

Although it is preferable that the convex portion 31 is formed into a circular dome shape, the convex portion 31 may be formed into an elliptical dome shape or a regular polygonal dome shape. The convex portions 31 may be formed by embossing the topsheet 22.

Next, the topsheet bonding portion 80 is described. As illustrated in FIG. 10 to FIG. 12-(b), when portions of the topsheet 22 between the adjacent convex portions 31 in the width direction and in the front and rear direction are pressed and welded (adhered) with the intermediate sheet 25, a number of topsheet bonding portions 80 are formed as intermittent bonding patterns in the width direction and in the front and rear direction. The topsheet bonding portion 80 is also a portion at which a bottom portion of the concave portion is formed.

In the bonding pattern of the topsheet 22 and the intermediate sheet 25 illustrated in FIG. 10 to FIG. 12-(b), in a region between the convex portions 31 that are adjacent in the MD direction, a line in which a plurality of topsheet bonding portions 80 are aligned in the CD direction with a space therebetween is formed to across a center position of the region in the CD direction. Further, at a space between the topsheet bonding portions 80 in the CD direction, the topsheet 22 and the intermediate sheet 25 are not welded and the topsheet 22 is formed as a pressed portion 81 that is more compressed than both sides in the MD direction.

Figure 13:
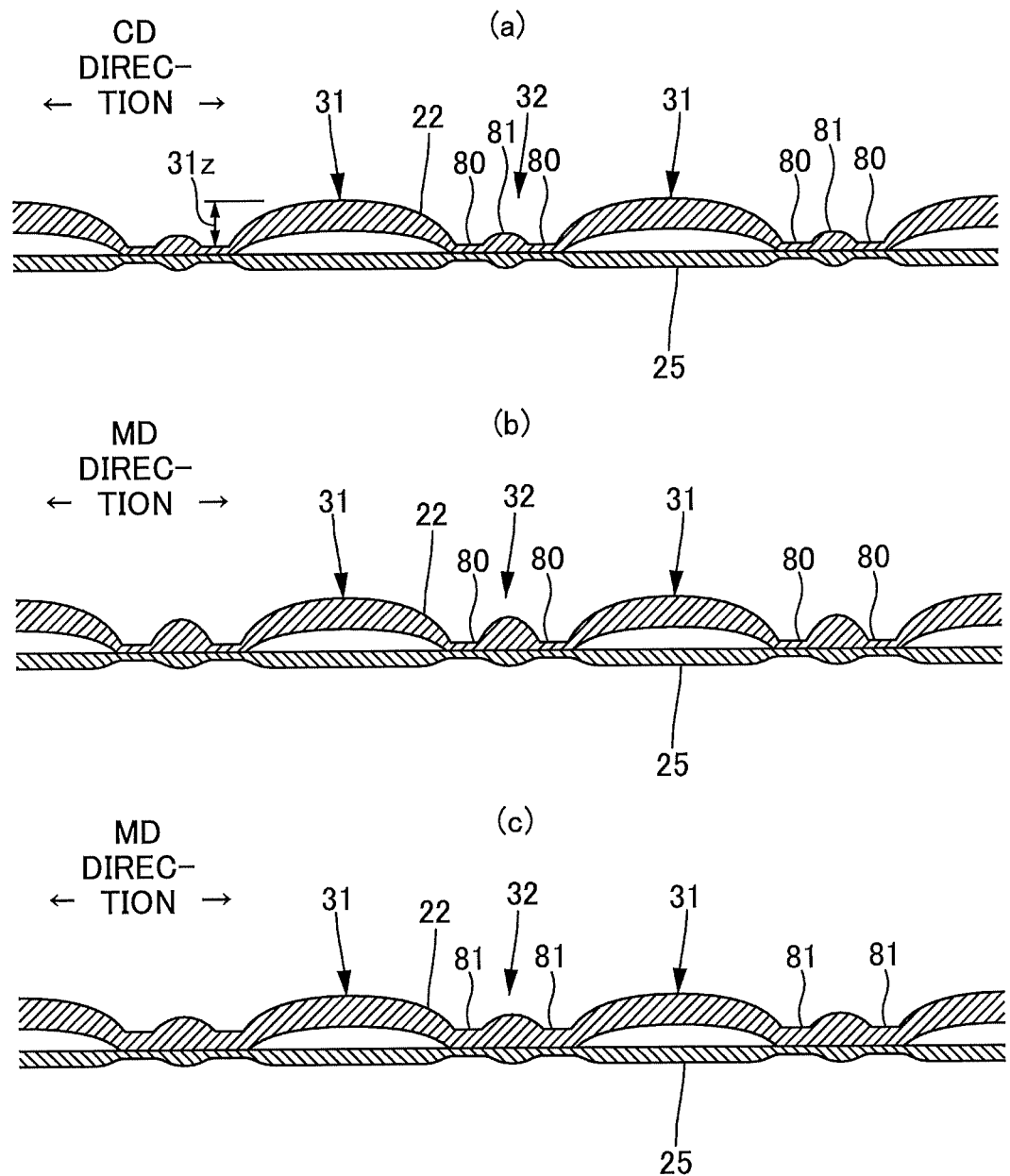
FIG. 13 is a cross-sectional view of FIG. 12-(b)

FIG. 13-(a), FIG. 13-(b) and FIG. 13-(c) are cross-sections of FIG. 12-(b) taken along 1-1, 2-2 and 3-3, respectively. As long as the topsheet 22 is pressed at the pressed portion 81, the intermediate sheet 25 may be integrally pressed with the topsheet 22, or may not be pressed. Further, although the topsheet 22 and the intermediate sheet 25 may not be welded and also may be pressed at portions other than the topsheet bonding portions 80 and the pressed portions 81 similarly as the space portions (81) in the CD direction, it is preferable that the topsheet 22 and the intermediate sheet 25 are not welded and also the topsheet 22 is pressed less than at the space portions in the CD direction (including a non-pressed state, where the topsheet 22 is not pressed at all).

In other words, when it is assumed that, in the topsheet 22, the thickness of the topsheet bonding portion 80 is T1, the thickness of the pressed portion 81 is T2 and the thickness of the portion other than the topsheet bonding portion 80 and the pressed portion 81 is T3, the relationship may be T1<T2=T3, but preferably, T1<T2<T3. Further, although a space is formed between a portion of the topsheet 22 that has the convex portion 31 and the intermediate sheet 25 in the embodiment illustrated in FIG. 13-(a) to FIG. 13-(c), such a space may not be formed, and in such a case, the entirety of the back surface of the topsheet 22 and the intermediate sheet 25 may be adhered.

Figure 15:
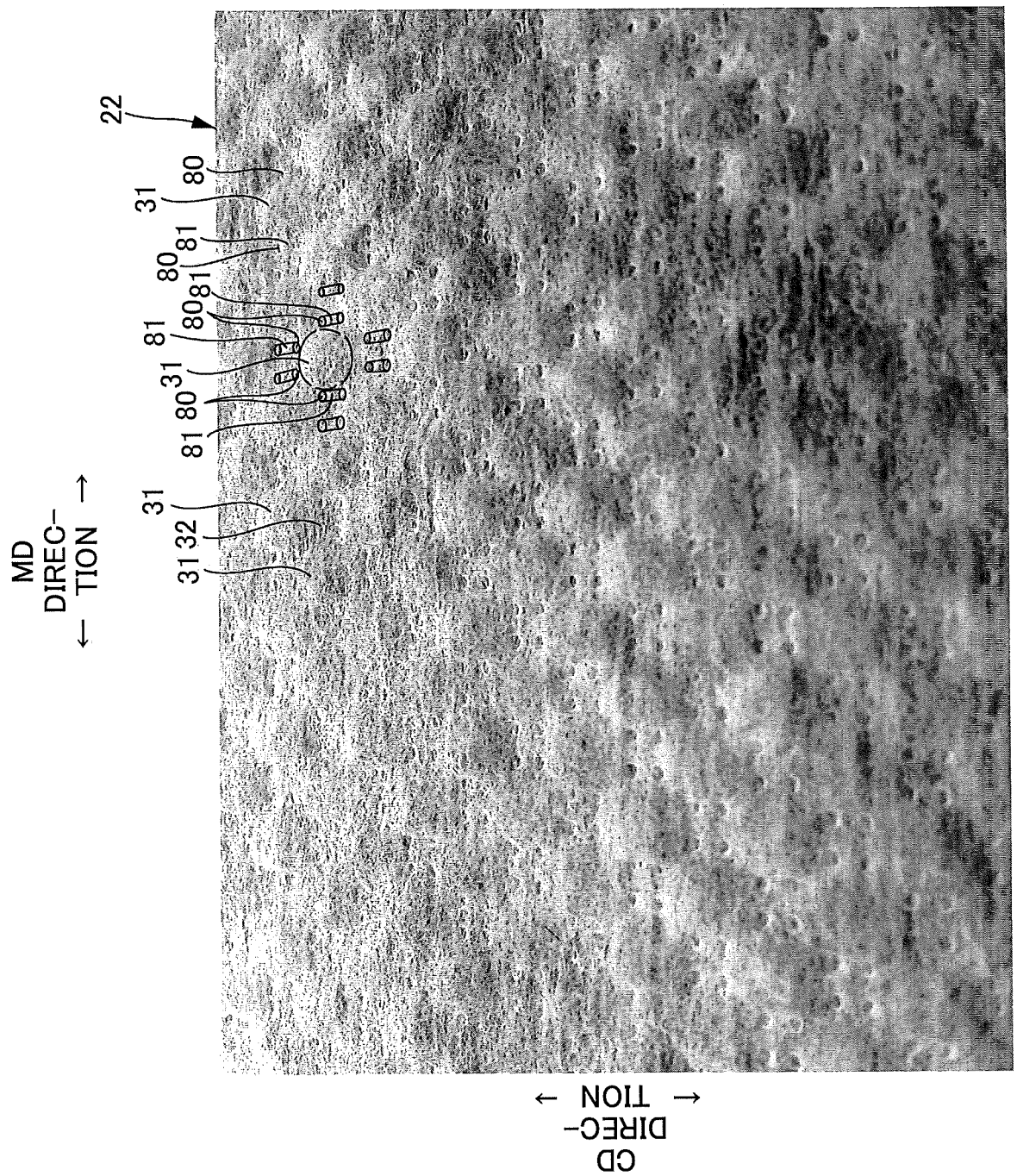
FIG. 15 is a picture taken from substantially top of an assembled body of the topsheet and the intermediate sheet.
Figure 16:
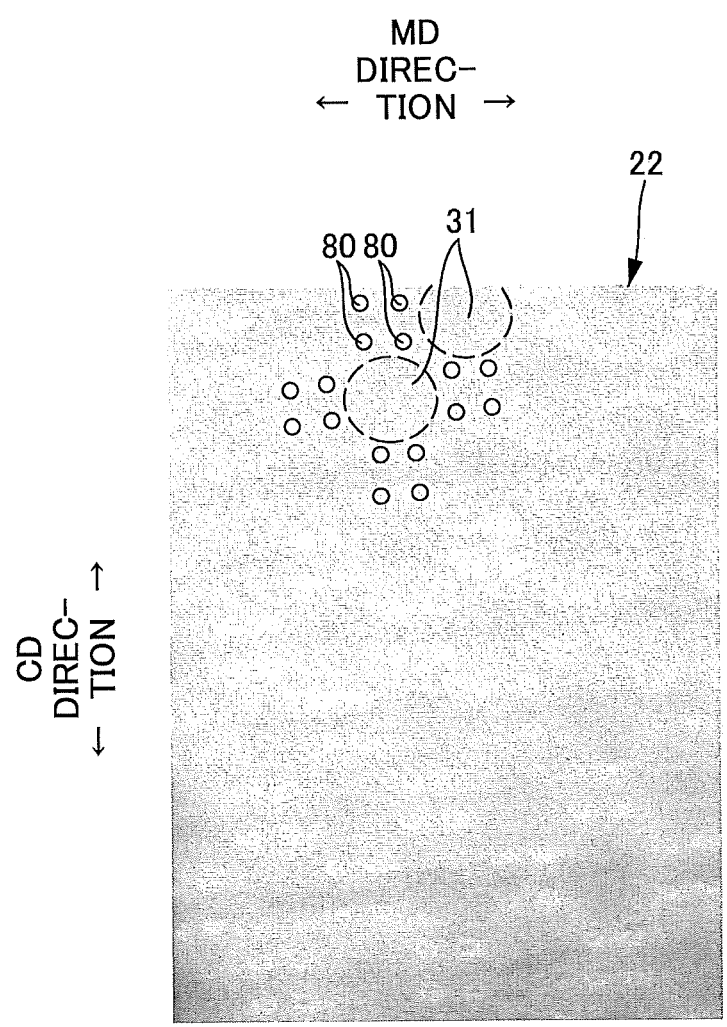
FIG. 16 is a picture of a surface of a topsheet of a comparative sample.

FIG. 15 illustrates a sample picture of an assembled body of the topsheet 22 and the intermediate sheet 25 in which the pattern illustrated in FIG. 10 and FIG. 12-(b) is adopted. FIG. 16 is a picture obtained by photographing a surface of a topsheet of a comparative sample.

As such, by adopting a characteristic bonding pattern at the space between the convex portions 31 that are adjacent in the MD direction, as is clear from the sample illustrated in FIG. 15 and the sample illustrated in FIG. 16, even when a vertical line (wrinkle) is formed when forming the convex portions 31, when bonding with the intermediate sheet 25, the topsheet bonding portions 80 by pressing and welding and the pressed portions 81 by pressing without welding are continuously alternately formed in the CD direction such that to across the vertical line. Thus, the topsheet bonding portions 80 can be formed to largely extend the vertical line, and such a state or a nearly state can be retained even after the product is manufactured. Further, as the finally bonded portions are intermittently provided in the CD direction, lowering of flexibility and worsening of an appearance can be prevented. On the other hand, in the comparative sample provided with the topsheet bonding portions 80 which do not satisfy the above described condition, a number of wrinkles each extending along the MD direction are formed with spaces in the CD direction, and an appearance is worsened.

The bonding pattern is not particularly limited as long as the plurality of topsheet bonding portions 80 are aligned in the CD direction with spaces their between at the region between the convex portions 31 that are adjacent in the MD direction, and the space between the topsheet bonding portions 80 in the CD direction is connected by the pressed portion 81. For example, as illustrated in FIG. 11-(*b*) FIG. 12-(*a*), it is preferable that the topsheet bonding portion 80 is also formed at a center position in the CD direction corresponding to a center portion in the CD direction between the convex portions 31 that are adjacent in the MD direction in order to prevent formation of wrinkles. In such a case, it is preferable to make an area of the topsheet bonding portion 80 at the center position in the CD direction to be smaller than those of other topsheet bonding portions 80 in a viewpoint of flexibility. Meanwhile, for example, as illustrated in FIG. 11-(*a*) and FIG. 12-(*b*), it is preferable to make a pattern in which the topsheet bonding portion 80 is not formed at the center position in the CD direction for improving flexibility.

Further, in addition to a case in which a single line of a plurality of the topsheet bonding portions 80 that are aligned with spaces in the CD direction is provided at the region between the convex portions 31 that are adjacent in the MD direction as illustrated in FIG. 11-(*a*) and FIG. 11-(*b*), a plurality of such lines may be provided with a space in the MD direction as illustrated in FIG. 10, FIG. 12-(*a*) and FIG. 12-(*b*). The former case is appropriate for the pattern in which the space between the convex portions 31 in the MD direction is narrow such as the embodiment where the convex portions 31 are aligned in a matrix form as illustrated in FIG. 11-(*a*) and FIG. 11-(*b*), and the latter case is appropriate for the pattern in which the space between the convex portions 31 in the MD direction is wide such as the embodiment where the convex portions 31 are aligned in a staggered form as illustrated in FIG. 10, FIG. 12-(*a*) and FIG. 12-(*b*). Here, for the latter embodiment, although the topsheet 22 and the intermediate sheet 25 may not be welded and pressed at the space portion of the topsheet bonding portions 80 in the MD direction similarly as the space portion in the CD direction, if the topsheet 22 and the intermediate sheet 25 are not welded and also the topsheet 22 is pressed less than the space portion in the CD direction (including a non-pressed state, where not pressed at all), better flexibility and appearance can be obtained.

The shape of each of the topsheet bonding portions is not specifically limited, and any shapes may be used such as an elliptical shape, a polygonal shape, a star shape, a cloud shape in addition to the circular shape as the illustrated example.

Although the size of the topsheet bonding portion 80 may be properly determined, it is preferable that each of the topsheet bonding portions 80 between the convex portions 31 that are adjacent in the MD direction is a point-like bonding portion whose length 80*m* in the MD direction is approximately 0.1 to 0.4 times (normally, 0.5 to 3 mm, for example) of a distance 31*y* in the MD direction between centers of the convex portions 31 of the CD direction lines that are adjacent in the MD direction, and whose length 80*c* in the CD direction is approximately 0.1 to 0.4 times (normally, 0.5 to 3 mm, for example) of a distance 31*x* in the CD direction between centers of the convex portions 31 of the MD direction lines that are adjacent in the CD direction. Further, it is preferable that a distance 80*d* in the CD direction between the topsheet bonding portions 80 that are adjacent in the CD direction is approximately 1 to 5 times (normally, 0.5 to 15 mm, for example) of the distance 80*c* in the CD direction of the topsheet bonding portion 80. It is preferable that the number of the topsheet bonding portions 80 in each of the CD direction lines is approximately 2 to 4.

Further, as illustrated in FIG. 12-(*a*) and FIG. 12-(*b*), when the convex portions 31 are formed in a staggered form, as the region between the convex portions 31 that are adjacent in the CD direction is also a region between the convex portions 31 that are adjacent in the MD direction, the topsheet bonding portions 80 similar to those provided between the convex portions 31 that are adjacent in the MD direction are provided. On the other hand, as illustrated in FIG. 11-(*a*) and FIG. 11-(*b*), when the convex portions 31 are formed in a matrix form, separately from the topsheet bonding portions 80 formed between the convex portions 31 that are adjacent in the MD direction, the topsheet bonding portions 80 are intermittently provided in the MD direction between the convex portions 31 that are adjacent in the CD direction. Although a pattern of the topsheet bonding portions 80 between the convex portions 31 that are adjacent in the CD direction is not specifically limited, it is preferable that the point-like topsheet bonding portions 80 are aligned with a space therebetween in the MD direction. As illustrated in FIG. 11-(*b*), similar to the space portion in the CD direction, the pressed portion 81 may be provided at a space portion in the MD direction. This MD direction line of the topsheet bonding portions 80 may be singularly provided at an intermediate position of the convex portions 31 that are adjacent in the CD direction as the illustrated example, and alternatively, a plurality of the MD direction lines of the topsheet bonding portions 80 may be provided with a space in the CD direction. Further, although the size of the point-like topsheet bonding portion 80 is not specifically limited, it is preferable that the length 80*m* in the MD direction is approximately 0.1 to 0.4 times (normally, 0.5 to 3 mm, for example) of the distance 31*y* between centers of the convex portions 31 of the CD direction lines that are adjacent in the MD direction, and the length 80*c* in the CD direction is approximately 0.1 to 0.4 times (normally, 0.5 to 3 mm, for example) of the distance 31*x* in the CD direction between centers of the convex portions 31 of the MD direction lines that are adjacent in the CD direction.

The topsheet bonding portions 80 are formed by intermittent bonding patterns in the width direction and in the front and rear direction, and a space in each of the directions may be properly determined. For example, it is preferable that a bonding range A3 in the CD direction by the topsheet bonding portions 80 between the convex portions 31 that are adjacent in the MD direction is approximately 0.3 to 1 times (normally, 1 to 10 mm, for example) of the distance 31*x* in the CD direction between centers of the convex portions 31 of the MD direction lines that are adjacent in the CD direction. Further, a bonding range A4 in the MD direction by the topsheet bonding portions 80 between the convex portions 31 that are adjacent in the CD direction is approximately 0.3 to 1 times (normally, 1 to 10 mm, for example) of the distance 31*y* in the MD direction between centers of the convex portions 31 of the CD direction lines that are adjacent in the MD direction. If these bonding range A3 in the CD direction and the bonding range A4 in the MD direction are too wide, such a structure is the same as a structure in which the topsheet bonding portions 80 are continuously formed in the CD direction and in the MD direction, respectively, and permeability and flexibility of the topsheet 22 may be lowered.

Figure 14:
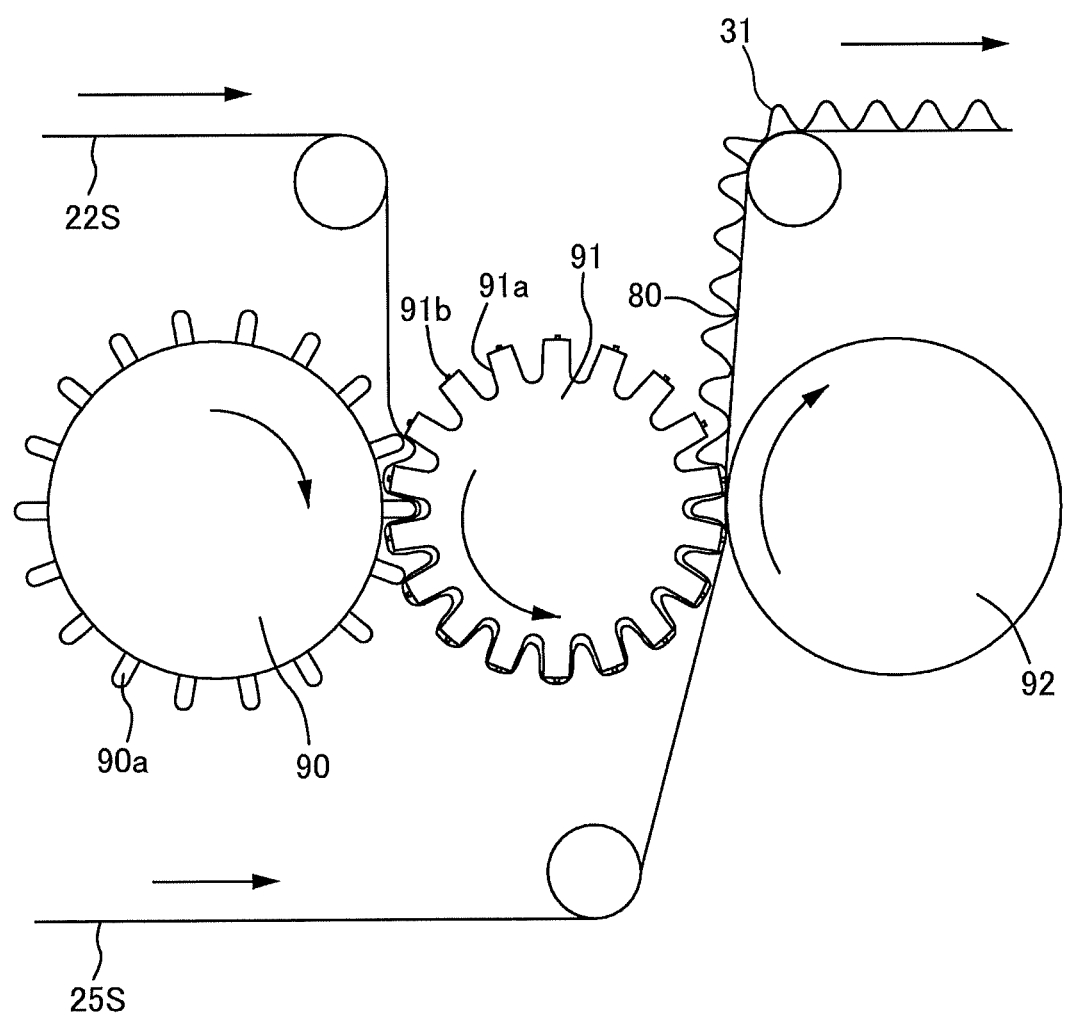
FIG. 14 is a view for describing an example of a processing plant of the topsheet and an intermediate sheet.

FIG. 14 illustrates a processing plant for forming the above described convex portions. The plant includes a pushing roller 90, a concave roller 91 facing the pushing roller 90, and a bonding roller 92 facing the concave roller 91. FIG. 17-(a) and FIG. 17-(b) are views illustrating the pushing roller 90. FIG. 18-(a) and FIG. 18-(b) are views illustrating the concave roller 91.

As illustrated in FIG. 17-(a) and FIG. 17-(b), a number of pushing convex portions 90a are formed at a peripheral surface of the pushing roller 90 in the above described alignment pattern of the convex portions 31. Although the shape of the convex portion of the pushing roller 90 may be properly determined, it is preferable that the shape is a frustum (circular truncated cone) having a cross-section (circular shape, elliptical shape, regular polygonal shape or the like, for example) corresponding to the shape of the convex portion 31 to be formed.

As illustrated in FIG. 18-(a) and FIG. 18-(b), pushdown concave portions 91a respectively corresponding to the pushing convex portions 90a of the pushing roller 90 are formed at a peripheral surface of the concave roller 91, and bonding convex portions 91b and a compressing convex portion 91e are formed between each adjacent pushdown concave portions 91a. The bonding convex portion 91b is a portion for forming the topsheet bonding portion 80 in the above described bonding pattern, and the compressing convex portion 91e is a portion for compressing a non-woven-fabric 22S which becomes the topsheet 22 in a thickness direction at a portion between the topsheet bonding portions 80 in the CD direction without welding the topsheet 22 and a material 25S of the intermediate sheet. When the material 25S of the intermediate sheet is one that is compressed in the thickness direction such as a non-woven-fabric, the intermediate sheet 25 is also compressed by the compressing convex portion 91e. More in detail, in this concave roller 91, at a region between the pushdown concave portions 91a that are adjacent in the circumferential direction of the roller, a line in which a plurality of the bonding convex portions 91b are aligned with a space in the axis direction of the roller is formed such that across a center position of the region in the axis direction of the roller, and a space portion between the bonding convex portions 91b in the axis direction of the roller is formed as the compressing convex portion 91e. Although the material is not compressed at portions other than the bonding convex portions 91b, the compressing convex portions 91e and the pushdown concave portions 91a, the portions may be compressed similarly as the compressing convex portions 91e or less than the compressing convex portions 91e. As long as the convex portion is formed, the pushdown concave portion 91a of the concave roller 91 may be an "open hole (aperture)" without a bottom surface having a size that the pushing convex portion can enter, and the "pushdown concave portion 91a" includes such an "open hole (aperture)".

The size, the shape and the arrangement of the pushing convex portion 90a of the pushing roller 90 correspond to the size, the shape and the arrangement of an inner space of the convex portion 31 to be formed, and the size, the shape and the arrangement of the pushdown concave portion 91a of the concave roller 91 correspond to the size, the shape and the arrangement of an outer shape of the convex portion 31 to be formed. Further, the size, the shape and the arrangement of the bonding convex portion 91b of the concave roller 91 correspond to the size, the shape and the arrangement of the topsheet bonding portion 80 to be formed, and the size, the shape and the arrangement of the compressing convex portion 91e of the concave roller 91 correspond to the size, the shape and the arrangement of the pressed portion 81 when the pressed portion 81 is formed. Thus, these size, shape and arrangement may be similarly changed to the size, the shape and the arrangement of the above described convex portion 31, the topsheet bonding portion and the pressed portion. For example, the length 91m in the MD direction, the length 91c in the CD direction and the distance 91d in the CD direction of the compressing convex portion 91c in the embodiment illustrated in FIG. 18-(b) may be within the ranges similar to the length 80m in the MD direction, the length 80c in the CD direction and the distance 80d in the CD direction of the topsheet bonding portion 80 illustrated in FIG. 12-(b).

Figure 19:
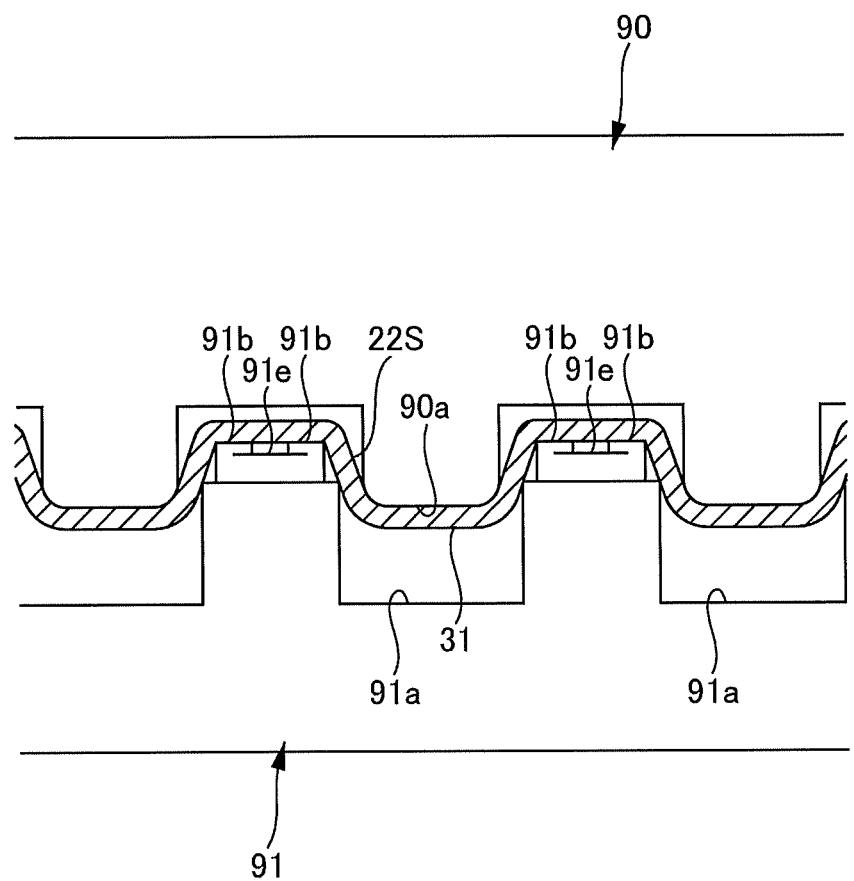
FIG. 19 is an enlarged cross-sectional view illustrating a main part of a forming step of a convex portion by the pushing roller and the concave roller.

FIG. 19 is an enlarged cross-sectional view illustrating a main part of a forming step of the convex portion by the pushing roller 90 and the concave roller 91. When processing, as illustrated in FIG. 19, the non-woven-fabric 22S which becomes the topsheet 22 is sandwiched between the pushing roller 90 and the concave roller 91 while transferring it by drawing from downstream of a manufacturing line, and the convex portions 31 are formed by embossing by which the convex portions of the pushing roller 90 are pushed into the pushdown concave portions 91a of the concave roller 91, respectively.

Thereafter, while guiding the non-woven-fabric 22S in which the convex portions 31 are formed by being wound around the concave roller 91, the material 25S of the intermediate sheet is transferred to outside of the non-woven-fabric which becomes the topsheet 22 by drawing from downstream of the manufacturing line. Then, as illustrated in FIG. 20-(a) and FIG. 20-(b), the non-woven-fabric 22S which becomes the topsheet 22 and the material 25S of the intermediate sheet are sandwiched between the concave roller 91 and the bonding roller 92, compressed between the compressing convex portions 91e of the concave roller 91 and the peripheral surface of the bonding roller 92, and heated to be welded between the bonding convex portions 91b of the concave roller 91 and the peripheral surface of the bonding roller 92. With this, the topsheet bonding portions 80 are formed, and an assembled body of the topsheet 22 and the intermediate sheet 25 is manufactured. With this, even when a vertical line (wrinkle) is formed in the non-woven-fabric 22S which becomes the topsheet 22 between the convex portions 31 that are adjacent in the MD direction when forming the convex portions 31, pressed and welded portions 80 and pressed portions 81 that are pressed but not welded are continuously alternately provided in the CD direction such that to across the vertical line, when bonding with the material 25S of the intermediate sheet. Thus, the topsheet bonding portions 80 can be formed to largely extend the vertical line, and such a state or a nearly state can be retained even after the product is manufactured. Further, as the finally bonded portions are intermittently provided in the CD direction, lowering of flexibility and worsening of an appearance can be prevented. Here, as can be understood from this principle, even when a trace compressed by the compressing convex portion 91e does not remain almost at all or does not remain at all, in addition to a case that the trace remains as the pressed portion 81, an effect of preventing the vertical line can be obtained.

Any pressing and welding means capable of pressing a material in its thickness direction and welding it may be adopted such as ultrasonic sealing in addition to heat seal by which a roller is heated to weld the material. A disposal diaper may be manufactured by imposing the processed assembled body of the topsheet 22 and the intermediate sheet 25 to an absorbent body and the like by a known method.

As described in the above embodiments, according to a processing method in which the topsheet is bonded with a material of the intermediate sheet 25 right after forming the convex portions 31 without having a period for absorbing a wrinkle, the wrinkle tends to remain more. Thus, it is preferable to adopt the above described bonding pattern. If the topsheet bonding portions 80 are formed after forming the convex portions 31 by embossing, another plant other than the above described processing plant including the three rollers. Further, although the non-woven-fabric that becomes the topsheet 22 is directly sent to a site where the pushing roller 90 and the concave roller 91 engage with each other in the illustrated example, the non-woven-fabric that becomes the topsheet 22 may be sent from a tangent line direction of the peripheral surface of the pushing roller 90 to be only wound around the pushing roller 90, and may be guided to transfer to the peripheral surface of the concave roller 91 while being sandwiched between the concave roller 91.

Description Regarding Terms in Specification

When following terms are used in the specification, unless otherwise described in the specification, the terms have following meanings, respectively.

The "front and rear (longitudinal) direction" means a direction connecting a ventral side (front side) and a dorsal side (rear side), and the "width direction" means a direction (lateral direction) that is perpendicular to the front and rear direction.

The "spread state" means a state evenly spread without contraction and looseness.

The "extension percentage" means a value assuming that its natural length is 100%.

The "weight per unit area" is measured as follows. After a sample or a test piece is preliminary dried, the sample or the like is left in a laboratory or an apparatus of a standard condition (temperature 20±5° C. and relative humidity less than or equal to 65% at the test place) to be constant mass. The preliminary drying means to make the sample or the test piece to be constant mass under environment in which the relative humidity is 10 to 25% and the temperature does not exceed 50° C. Here, for the fiber whose official moisture regain is 0.0%, it is unnecessary to perform the preliminary drying. A sample whose size is 200 mm×250 mm (±2 mm) is cut from the test piece at the constant mass using a paper density plate (200 mm×250 mm, ±2 mm). The gravity of the sample is measured, and weight per unit area is obtained by multiplying the measured value by 20 times and calculating the weight per square meter.

The "thickness" of each of the topsheet 22 and the intermediate sheet 25 illustrated in FIG. 10 to FIG. 20-($b$) means an apparent thickness, and is measured by a method described at paragraph 0017 of Japanese Patent No. 3611838. Specifically, when measuring, a measurement piece of length 30 mm×width 30 mm is cut under a state that the topsheet 22 and the intermediate sheet 25 are bonded. Then, a cut surface is formed by a line that is substantially in parallel to a vertical line (a fiber orientation direction (a flowing direction in manufacturing the non-woven-fabric) of a non-woven-fabric (fiber aggregation) that constitutes the topsheet 22) and also passes on the topsheet bonding portion 80. An enlarged picture of this cut surface is obtained by a digital microscope VHX-1000 manufactured by KEYENCE CORPORATION or the like, an apparent maximum thickness of the topsheet 22 is obtained based on this enlarged picture as the thickness of the topsheet 22, and an apparent thickness of the intermediate sheet 25 is measured at a measurement site of the maximum thickness of the topsheet 22 as the thickness of the intermediate sheet 25. Further, the size in the cross-sectional direction such as the thickness of other sites (the thickness of the topsheet bonding portion 80, the thickness of the pressed portion 81 and the like) or the height 31$z$ of the convex portion 31 is measured similarly as the measurement of the "thickness" of the topsheet and the intermediate sheet and the protrusion height of the convex portion from a bottom portion to a top portion (an apex) is measured.

The "thickness" of the absorbent body is measured using a thickness gauge (PEACOCK, Large type Dial Thickness Gauge, J-B (measurement range 0 to 35 mm) or K-4 (measurement range 0 to 50 mm)) manufactured by OZAKI MFG. CO., LTD. while horizontally maintaining the sample and the thickness gauge.

The "thickness" other than above is automatically measured using an automatic thickness gauge (KES-G5 handy compression measurement program) under a condition of load: 10 gf/cm$^2$, and pressed area: 2 cm$^2$.

When an environmental condition of a test or a measurement is not described, it is assumed that the test or the measurement is conducted in a laboratory or an apparatus under a standard condition (temperature 20 ±5° C. and relative humidity less than or equal to 65% at the test place).

The size of each part means the size at the spread state, not a natural length, unless otherwise described.

Hereinafter, preferable embodiments of the invention are described.

Clause 1

An absorbent article including:
a crotch portion;
a front side portion and a rear side portion that are extended toward a front side and a rear side of the crotch portion, respectively; and
an absorbent body provided at least at the crotch portion,
wherein a pair of slits each extending in a front and rear direction with a predetermined width is formed in the absorbent body at a front and rear direction region at least at the crotch portion so as to section a first portion positioned at middle in a width direction, and a second portion and a third portion positioned at both sides of the first portion in the width direction, respectively,
wherein the absorbent body includes projection portions projected toward both sides in the width direction at middle in the front and rear direction of the first portion, and
wherein cavity portions in which the projection portions fit outwardly in the width direction are formed at a front and rear direction position corresponding to the projection portions in the second portion and the third portion, respectively.

Effects

According to the absorbent article of the invention, the projection portions projected toward both sides in the width direction are provided in the first portion sectioned by the slits, and the cavity portion in which the projection portions fit outwardly in the width direction are formed at a front and rear direction position corresponding to the projection portions in the second portion and the third portion, respectively, at the both sides in the width direction of the first portion. With this configuration, when the crotch portion is sandwiched by both legs of a wearer at a worn state and the crotch portion is contracted in the width direction to a certain extent so that both sides of the slits are close to each other, the projection portions of the first portion fit into the cavity portion of the second portion and the cavity portion of the third portion, respectively (including an embodiment in which the projection portions loosely fit), and integration between a portion between the slits and laterally outer portions of the slits, Thus, the slit forming region of the absorbent body is hardly deformed by movement of the legs, twisting or tearing hardly occurs and the shape of the slits hardly changes.

Here, the term "slit" means a portion that penetrates a top surface to a back surface of the absorbent body. Further, "with a predetermined width" regarding the slit just means that a slit that does not have a width (a case when the facing side walls contact) is not included, and does not mean that the width of the slit is constant. Thus, as long as the slit includes a width, a slit whose width varies is also included.

Clause 2

The absorbent article according to clause 1, wherein the cavity portions are groove-like portions that are formed at back surfaces of the second portion and the third portion to extend from side edges at a first portion side outwardly in the width direction, respectively.

Effects

When the cavity portions are such groove-like portions, the projection portions of the first portion can fit into the cavity portion of the second portion and the cavity portion of the third portion while the second portion and the third portion are positioned above the first portion, respectively. At this time, as a space is formed between the second portion and the third portion, a groove whose side portions are the second portion and the third portion and whose bottom portion is the first portion is formed to extend in the front and rear direction, or even when the second portion and the third portion contact, a small groove that extend along the front and rear direction is formed at their interface. Thus, even when the slits are collapsed as the crotch portion is pressed in the width direction, lowering of diffusibility in the front and rear direction can be suppressed.

Clause 3

The absorbent article according to clause 2, wherein a portion of the first portion between the projection portions is formed as a movement stop portion in which at least an intermediate portion in the width direction is protruded toward a top surface with respect to both sides of the intermediate portion in the width direction.

Effects

By providing such a movement stop portion, when projection portions of the first portion respectively fit the cavity portion of the second portion and the cavity portion of the third portion while the second portion and the third portion are positioned above the first portion, the second portion and the third portion knock against the movement stop portion without moving to opposite sides. In other words, the second portion and the third portion are prevented from being positioned too close to a center in the width direction after being positioned above the first portion.

Clause 4

The absorbent article according to claim 2 or 3, wherein, at a surface, regions corresponding to at least both side portions of the first portion, and regions that are adjacent to them at outsides in the width direction are formed to be concavo-convex surfaces, respectively, in each of which a number of convex portions are aligned with a space therebetween in each of the width direction and the front and rear direction, and wherein the convex portions of the concavo-convex surfaces are formed such that the concavo-convex surfaces of the regions corresponding to at least the both side portions of the first portion, and the concavo-convex surfaces of the regions that are adjacent to them at outsides in the width direction engage with each other, respectively.

Effects

As described above, when the second portion and the third portion are positioned above the first portion, the regions that are adjacent to the regions corresponding to the both side portions of the first portion at outsides in the width direction contact the surfaces of the regions corresponding to the both side portions of the first portion while being turned over. At this time, when the facing contacting surfaces are formed as the concavo-convex surfaces that are capable of engaging with each other as described above, integration between the second portion and the third portion with the first portion under the state that the second portion and the third portion are positioned above can be furthermore improved. Here, the concavo-convex surfaces are "engaging with each other" means that at least an apex of each of the convex portions of one of the facing surfaces gets into a space between the convex portions of the other of the facing surfaces.

INDUSTRIAL APPLICABILITY

The present invention can be used for a general absorbent article such as a sanitary napkin in addition to a disposal diaper such as a pad type disposal diaper, a pull-up type or a tape type disposal diaper.

The present application is based on and claims the benefit of priority of Japanese Priority Application No. 2015-181530 filed on Sep. 15, 2015, the entire contents of which are hereby incorporated by reference.

NUMERALS

B2 . . . rear side portion, C2 . . . crotch portion, F2 . . . front side portion, 11 . . . first portion, 12 . . . second portion or third portion, 21 . . . liquid impermeable sheet, 22 . . . topsheet, 23 . . . absorbent body, 23C . . . movement stop portion, 23D . . . cavity portion, 23P . . . projection portion, 24 . . . standing gather, 24s . . . gather sheet, 25 . . . intermediate sheet, 26 . . . packaging sheet, 27 . . . exterior sheet, 31 . . . convex portion, 40 . . . slit, 41 . . . another slit, 200 . . . pad type disposal diaper.

What is claimed is:

1. An absorbent article comprising:
a crotch portion;
a front side portion and a rear side portion that are extended toward a front side and a rear side of the crotch portion, respectively; and
an absorbent body provided at least at the crotch portion,
wherein a pair of slits each extending in a front and rear direction with a predetermined width is formed in the absorbent body at a front and rear direction region at least at the crotch portion so as to section a first portion positioned at middle in a width direction, and a second portion and a third portion positioned at both sides of the first portion in the width direction, respectively,
wherein the absorbent body includes projection portions projected toward both sides in the width direction at middle in the front and rear direction of the first portion, and
wherein cavity portions in which the projection portions fit outwardly in the width direction are formed at a front and rear direction position corresponding to the projection portions in the second portion and the third portion, respectively,
wherein the cavity portions are groove-like portions that are formed at back surfaces of the second portion and the third portion to extend from side edges at a first portion side outwardly in the width direction, respectively,
wherein, at a surface, regions corresponding to at least both side portions of the first portion, and regions that are adjacent to them at outsides in the width direction are formed to be concavo-convex surfaces, respectively, in each of which a number of convex portions are aligned with a space therebetween in each of the width direction and the front and rear direction, and
wherein the convex portions of the concavo-convex surfaces are formed such that the concavo-convex surfaces of the regions corresponding to at least the both side portions of the first portion, and the concavo-convex surfaces of the regions that are adjacent to them at outsides in the width direction engage with each other, respectively.

2. The absorbent article according to claim 1, wherein a portion of the first portion between the projection portions is formed as a movement stop portion in which at least an intermediate portion in the width direction is protruded toward a top surface with respect to both sides of the intermediate portion in the width direction.

* * * * *